(12) United States Patent
Li et al.

(10) Patent No.: US 8,420,626 B2
(45) Date of Patent: Apr. 16, 2013

(54) ARENE CONNECTED POLYAMINE MACROCYCLIC DERIVATIVES, PREPARATION METHODS AND PHARMACEUTICAL USES THEREOF

(75) Inventors: Song Li, Beijing (CN); Jing Su, Beijing (CN); Yao Liu, Beijing (CN); Junhai Xiao, Beijing (CN); Lili Wang, Beijing (CN); Wu Zhong, Beijing (CN); Zhibing Zheng, Beijing (CN); Yunde Xie, Beijing (CN); Xingzhou Li, Beijing (CN); Guoming Zhao, Beijing (CN); Xiaokui Wang, Beijing (CN); Xinbo Zhou, Beijing (CN); Hongying Liu, Beijing (CN)

(73) Assignee: Beijing Molecule Science and Technology Co., Ltd., Beijing (CN)

( * ) Notice: Subject to any disclaimer, the term of this patent is extended or adjusted under 35 U.S.C. 154(b) by 397 days.

(21) Appl. No.: 12/601,867

(22) PCT Filed: May 30, 2008

(86) PCT No.: PCT/CN2008/001070
§ 371 (c)(1),
(2), (4) Date: Feb. 22, 2010

(87) PCT Pub. No.: WO2008/148302
PCT Pub. Date: Dec. 11, 2008

(65) Prior Publication Data
US 2010/0179116 A1    Jul. 15, 2010

(30) Foreign Application Priority Data
May 30, 2007    (CN) .......................... 2007 1 0106045

(51) Int. Cl.
| *A61K 31/33* | (2006.01) |
| *C07D 245/00* | (2006.01) |
| *C07D 245/02* | (2006.01) |
| *C07D 245/04* | (2006.01) |
| *C07D 245/06* | (2006.01) |
| *C07D 487/02* | (2006.01) |

(52) U.S. Cl.
USPC .......................... 514/183; 540/470; 540/473

(58) Field of Classification Search .................. None
See application file for complete search history.

(56) References Cited

U.S. PATENT DOCUMENTS
3,373,077 A    3/1968    O'Connell

FOREIGN PATENT DOCUMENTS
| JP | 04212968 | * | 8/1992 |
| WO | WO2004014316 A2 | | 2/2004 |
| WO | WO2004014317 A2 | | 2/2004 |

OTHER PUBLICATIONS

Rodriguez-Spong. Advanced Drug Delivery Reviews, 2004, 56, 241-274.*
"Acquired Immunodefficiency Syndrome Symptoms, Causes, Treatment", http://www.medicinenet.com/acquired_immunodeficiency_syndrome_aids/page9.htm, accessed Feb. 2, 2012.*
UNAIDS. HIV-related opportunistic diseases, 1998, 2-10.*
Wu. Chinese Journal of Polymer Science, 2001, 19(5), 455-466.*
European Search Report, EP08772919, dated Jul. 6, 2011.
Jing, Su et al., Synthesis of Aromatic-linked polyamine macrocyclic derivatives as HIV-1 entry inhibitors, Chinese Chemical Letters, vol. 18, 2007, pp. 1166-1168.
Wallon, Alexander et al., Pentamacrocyclic tris-crown hosts: selective binding of cationic, anionic, and neutral guests, Journal of the Chemical Society, Chemical Communications, vol. 123, 1990, pp. 859-867.
International Search Report for International Application No. PCT/CN2008/001070, Date of mailing Sep. 4, 2008.

* cited by examiner

Primary Examiner — Noble Jarrell
(74) Attorney, Agent, or Firm — MacMillan, Sobanski & Todd, LLC

(57) ABSTRACT

The present invention relates to arene connected polyamine macrocyclic derivatives represented by general formula I, pharmaceutically acceptable salts or hydrates thereof which have anti-HIV activities, in which the definitions of substituents are as defined in the description; to preparation methods of the compounds of formula I; to pharmaceutical compositions containing the compounds of formula I or their pharmaceutically acceptable salts or hydrates; to the use of the compounds of formula I or their pharmaceutically acceptable salts or hydrates for the preparation of a medicament for the treatment and prevention of HIV-associated diseases.

7 Claims, No Drawings

ARENE CONNECTED POLYAMINE MACROCYCLIC DERIVATIVES, PREPARATION METHODS AND PHARMACEUTICAL USES THEREOF

TECHNICAL FIELD

The present invention relates to arene connected polyamine macrocyclic derivatives or pharmaceutically acceptable salts thereof, their preparation methods, pharmaceutical compositions containing the compounds and the use of the compounds for the preparation of a medicament for the treatment HIV infectious diseases or conditions.

BACKGROUND ART

Acquired immune deficiency syndrome (AIDS) is a diseased induced by HIV. At present, a large number of persons have been infected with this disease. Thus, this disease has been studied widely.

Studies on medicaments for the treatment and prevention of AIDS have been important contents in the research on the treatment of AIDS. In terms of the biological characteristics of HIV, the present studies on anti-HIV medicaments are mainly in the development of effective therapeutic medicaments to the key enzyme during the replication of HIV-HIV reverse transcriptase (HIVRT) and HIV proteinase (HIVPR). The former is also divided into nucleoside HIVRT inhibitors (NRTI) and non-nucleoside HIVRT inhibitors (NNRTI). The main studies are focused on nucleoside analogues, proteinase inhibitors, integrase inhibitors, etc. If reverse transcriptase and proteinase inhibitors are administered for too long time, not only severe toxicity and many complications are caused, but also the patients will generate drug-resistance in vivo, and therapeutic effects are very limited. There is also another important enzyme during HIV replication-integrase, which integrates viral genomes into host cell chromosomes, so that the viruses are incubated in vivo for long term. Integrase is a characteristic enzyme of HIV itself and also an ideal target for designing of anti-HIV drugs. At present, the studies on this aspect are mainly focused on DNA binders and topoisomerase inhibitors, nucleosides, peptides, polyhydroxylated aromatic compounds and so on. However, the structure of HIV integrase has not been clarified yet, and the structure, function and biology of the integrase still have defects. Further, the crystalline structure of total length integrase and the crystalline structure when enzymes bind with inhibitors, with substrate DNA, and with divalent metallic ions have not been known yet. Thus, it is difficult to effectively develop medicaments for the treatment and prevention of AIDS.

Except that the enzyme which is indispensable for self-replication of HIV virus is the action target of anti-HIV drugs, fused proteins of HIV virus are also important action target. The infection of HIV to cells can be inhibited through interception of fusion of HIV virus so as to achieve effective treatment of AIDS. HIV fused protein gp41 is an important ingredient of surface fused proteins of HIV virus and will generate conformational variation during fusion, six bands α-spiral contained in the structure thereof fold to form hairpin structure. Such conformational variation renders that the membrane of viruses and cellular membranes get close to a proper position so as to benefit the carrying out of fusion. Up-to-date study results have shown that if the formation of hairpin structure of HIV fused protein gp41 can be inhibited effectively, the fusion of HIV to cellular membranes can be also prevented.

Therefore, it is possible to develop the research of HIV fused protein inhibitors based on the formation sites of gp41 hairpin structure. The inhibition of HIV membrane fusion can achieved by developing inhibitors to intercept the formation of the hairpin structure so as to finally realize the effective treatment of AIDS.

SUMMARY OF THE INVENTION

The purpose of the invention is to seek and develop compounds having anti-HIV activity for the treatment of AIDS and conditions associated with AIDS as well as other diseases caused by retro viruses.

The inventor has found that compounds of formula I can be used for the treatment and prevention of HIV infectious diseases.

Therefore, the invention at one aspect provides a compound of formula I,

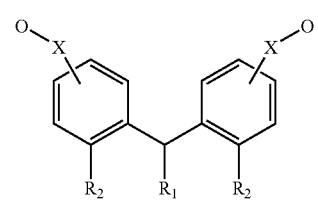

wherein:

O represents a macro ring having 9 to 20 atoms, in which each macro ring contains 3 to 6 nitrogen atoms;

$R_1$ represents a radical selected from the group consisting of: hydrogen, halogen; perfluoroalkyl; alkoxyalkyl; amino; alkylamino; dialkylamino; amido; alkylaminoalkyl; unsubstituted or substituted, saturated or unsaturated straight or branched alkyl; carboxyl; substituted or unsubstituted phenyl, the substituents of the phenyl being at least one radical selected from the group consisting of: hydroxyl, alkoxy, alkoxyalkyl, halogen, perfluoroalkyl, thio, nitro, carboxyalkyl, alkoxycarbonyl, alkoxycarbonylalkyl, carboxyamido, carboxyamidoalkyl, alkyl, cycloalkyl, alkylthio, alkylsulfinyl, alkylsulfonyl, aminosulfonyl, amidino, cyano, amino, amido, alkylamino, dialkylamino, alkylaminoalkyl, or alkoxy mono-substituted by substituent selected from the group consisting of carboxyl, amino, alkylamino or dialkylamino; cycloalkyl; or heterocyclic radical selected from the group consisting of: pyridyl, thienyl, pyrazolyl, tetrazolyl, furyl, pyrrolyl, imidazolyl, triazolyl and thiazolyl, including isomers and substituted heterocyclic rings of all positions of the heterocyclic radical;

$R_2$ represents a radical selected from the group consisting of: hydrogen, hydroxyl, mercapto, alkoxy, carboxyl, carboxyalkyl, amino, alkylamino, dialkylamino, carboxyamido, carboxyamidoalkyl, aminosulfonyl or acetamido;

X represents a linking radical selected from the group consisting of: —N=CH—, —CH=N—, —$(CH_2)_n$—NH—, —NH—$(CH_2)$—, —$(CH_2)_n$—, —CH=CH— or —N=N—, n is an integer from 1 to 8, racemes or optical isomers thereof, or pharmaceutically acceptable salts and solvates thereof.

The compound of formula I is particularly preferably the compounds as shown below:

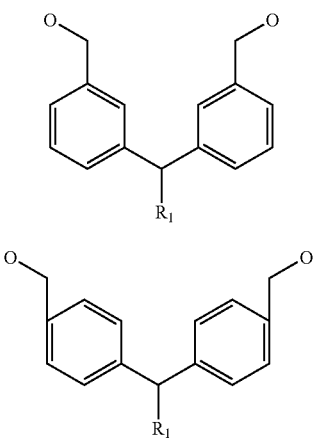

II

III wherein:

O represents a macro ring having 9 to 20 atoms, in which each macro ring contains 3 to 6 nitrogen atoms;

$R_1$ represents a radical selected from the group consisting of: hydrogen, halogen; perfluoroalkyl; alkoxyalkyl; amino; alkylamino; dialkylamino; amido; alkylaminoalkyl; unsubstituted or substituted, saturated or unsaturated straight or branched alkyl; carboxyl; substituted or unsubstituted phenyl, the substituents of the phenyl being at least one radical selected from the group consisting of: hydroxyl, alkoxy, alkoxyalkyl, halogen, perfluoroalkyl, thio, nitro, carboxyalkyl, alkoxycarbonyl, alkoxycarbonylalkyl, carboxyamido, carboxyamidoalkyl, alkyl, cycloalkyl, alkylthio, alkylsulfinyl, alkylsulfonyl, aminosulfonyl, amidino, cyano, amino, amido, alkylamino, dialkylamino, alkylaminoalkyl, or alkoxy mono-substituted by substituent selected from the group consisting of carboxyl, amino, alkylamino or dialkylamino; cycloalkyl; or heterocyclic radical selected from the group consisting of: pyridyl, thienyl, pyrazolyl, tetrazolyl, furyl, pyrrolyl, imidazolyl, triazolyl and thiazolyl, including isomers and substituted heterocyclic rings of all positions of the heterocyclic radical.

According to another aspect, the invention provides an intermediate for the preparation of a compound of formula I according to the invention. This intermediate has general formula as follows:

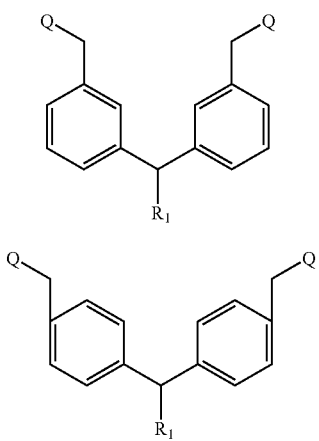

IV

V wherein:

Q represents halogen atom;

$R_1$ represents a radical selected from the group consisting of: hydrogen, halogen; perfluoroalkyl; alkoxyalkyl; amino; alkylamino; dialkylamino; amido; alkylaminoalkyl; unsubstituted or substituted, saturated or unsaturated straight or branched alkyl; carboxyl; substituted or unsubstituted phenyl, the substituents of the phenyl being at least one radical selected from the group consisting of: hydroxyl, alkoxy, alkoxyalkyl, halogen, perfluoroalkyl, thio, nitro, carboxyalkyl, alkoxycarbonyl, alkoxycarbonylalkyl, carboxyamido, carboxyamidoalkyl, alkyl, cycloalkyl, alkylthio, alkylsulfinyl, alkylsulfonyl, aminosulfonyl, amidino, cyano, amino, amido, alkylamino, dialkylamino, alkylaminoalkyl, or alkoxy mono-substituted by substituent selected from the group consisting of carboxyl, amino, alkylamino or dialkylamino; cycloalkyl; or heterocyclic radical selected from the group consisting of: pyridyl, thienyl, pyrazolyl, tetrazolyl, furyl, pyrrolyl, imidazolyl, triazolyl and thiazolyl, including isomers and substituted heterocyclic rings of all positions of the heterocyclic radical.

According to the invention, in the terms "perfluoroalkyl, alkyl" in the specification and claims, alkyl means $C_{1-6}$alkyl containing from 1 to 6 carbon atoms.

According to the invention, in the terms "alkoxy, alkoxyalkyl alkoxycarbonyl, alkoxycarbonylalkyl", alkoxy generally means $C_{1-6}$alkoxy containing 1 to 6 carbon atoms, and alkyl means $C_{1-6}$alkyl containing 1 to 6 carbon atoms.

According to the invention, in the terms "alkylamino, dialkylamino, alkylaminoalkyl", the alkyl moiety of alkylamino means $C_{1-6}$alkyl containing 1 to 6 carbon atoms, and alkyl means $C_{1-6}$alkyl containing 1 to 6 carbon atoms.

According to the invention, the acyl moiety in the term "acetamido" means an acyl containing 1 to 6 carbon atoms.

According to the invention, the terms "carboxyamido, carboxyamidoalkyl" include but are not limited to $C_{1-6}$-carboxyamido or $C_{1-6}$-carboxyamido $C_{1-6}$alkyl.

According to the invention, the terms "alkylthio, alkylsulfinyl, alkylsulfonyl" include but are not limited to $C_{1-6}$alkylthio, $C_{1-6}$alkylsulfinyl, $C_{1-6}$alkylsulfonyl.

According to the invention, the term "cycloalkyl" includes but is not limited to $C_{3-8}$cycloalkyl.

According to the invention, the term "macro ring having 9 to 20 atoms, in which each macro ring contains 3 to 6 nitrogen atoms" includes but is not limited to:
(1,4,8,11-tetraazacyclotetradecan-1-yl);
(1,4,7,10-tetraazacyclododecan-1-yl);
[3,7,11-triaza-dicyclo[11.3.1]heptadecan-1(16),13(17),14-trien-7-yl];
[3,7,11,17-tetraaza-dicyclo[11.3.1]heptadecan-1(16),13(17),14-trien-7-yl].

The preferred compounds of the invention include:
3,3'-bis[(1,4,8,11-tetraazacyclotetradecan-1-yl)-methyl]-1,1',1"-triphenylmethane;
3,3'-bis[(1,4,8,11-tetraazacyclotetradecan-1-yl)-methyl]-4"-methyl-1,1',1"-triphenylmethane;
3,3'-bis[(1,4,8,11-tetraazacyclotetradecan-1-yl)-methyl]-4"-bromo-1,1',1"-triphenylmethane;
3,3'-bis[(1,4,8,11-tetraazacyclotetradecan-1-yl)-methyl]-4"-fluoro-1,1',1"-triphenylmethane;
3,3'-bis[(1,4,8,11-tetraazacyclotetradecan-1-yl)-methyl]-3"-chloro-1,1',1"-triphenylmethane;
2-{[3,3'-bis[(1,4,8,11-tetraazacyclotetradecan-1-yl)-methyl]-1,1'yl]-diphenyl}methylene pyridine;
4,4'-bis[(1,4,8,11-tetraazacyclotetradecan-1-yl)-methyl]-1,1',1"-triphenylmethane;
4,4'-bis[(1,4,8,11-tetraazacyclotetradecan-1-yl)-methyl]-4"-methyl-1,1',1"-triphenylmethane;

4,4'-bis[(1,4,8,11-tetraazacyclotetradecan-1-yl)-methyl]-4"-bromo-1,1',1"-triphenylmethane;

4,4'-bis[(1,4,8,11-tetraazacyclotetradecan-1-yl)-methyl]-4"-fluoro-1,1',1"-triphenylmethane;

4,4'-bis[(1,4,8,11-tetraazacyclotetradecan-1-yl)-methyl]-3"-chloro-1,1',1"-triphenylmethane;

3,3'-bis[(1,4,7,10-tetraazacyclododecan-1-yl)-methyl]-1,1',1"-triphenylmethane octahydrochloride;

3,3'-bis{[3,7,11-triaza-dicyclo[11.3.1]heptadecan-1(16),13(17),14-trien-7-yl]-methyl}-1,1',1"-triphenylmethane;

3,3'-bis{[3,7,11-triaza-dicyclo[11.3.1]heptadecan-1(16),13(17),14-trien-7-yl]-methyl}-4"-methyl-1,1',1"-triphenylmethane;

3,3'-bis{[3,7,11-triaza-dicyclo[11.3.1]heptadecan-1(16),13(17),14-trien-7-yl]-methyl}-4"-bromo-1,1',1"-triphenylmethane;

3,3'-bis{[3,7,11-triaza-dicyclo[11.3.1]heptadecan-1(16),13(17),14-trien-7-yl]-methyl}-4"-fluoro-1,1',1"-triphenylmethane;

3,3'-bis{[3,7,11-triaza-dicyclo[11.3.1]heptadecan-1(16),13(17),14-trien-7-yl]-methyl}-3"-chloro-1,1',1"-triphenylmethane;

2-{[3,3'-bis((3,7,11-triaza-dicyclo[11.3.1]heptadecan-1(16),13(17),14-trien-7-yl)-methyl)-1,1'yl]-diphenyl}methylene pyridine;

3,3'-bis{[3,7,11,17-tetraaza-dicyclo[11.3.1]heptadecan-1(16),13(17),14-trien-7-yl]-methyl}-1,1',1"-triphenylmethane;

3,3'-bis{[3,7,11,17-tetraaza-dicyclo[11.3.1]heptadecan-1(16),13(17),14-trien-7-yl]-methyl}-4"-methyl-1,1',1"-triphenylmethane;

3,3'-bis{[3,7,11,17-tetraaza-dicyclo[11.3.1]heptadecan-1(16),13(17),14-trien-7-yl]-methyl}-4"-bromo-1,1',1"-triphenylmethane;

3,3'-bis{[3,7,11,17-tetraaza-dicyclo[11.3.1]heptadecan-1(16),13(17),14-trien-7-yl]-methyl}-4"-fluoro-1,1',1"-triphenylmethane;

3,3'-bis{[3,7,11,17-tetraaza-dicyclo[11.3.1]heptadecan-1(16),13(17),14-trien-7-yl]-methyl}-3"-chloro-1,1',1"-triphenylmethane;

2-{[3,3'-bis((3,7,11,17-tetraaza-dicyclo[11.3.1]heptadecan-1(16),13(17),14-trien-7-yl)-methyl)-1,1'yl]-diphenyl}methylene pyridine;

4,4'-bis{[3,7,11-triaza-dicyclo[11.3.1]heptadecan-1(16),13(17),14-trien-7-yl]-methyl}-1,1',1"-triphenylmethane;

4,4'-bis{[3,7,11-triaza-dicyclo[11.3.1]heptadecan-1(16),13(17),14-trien-7-yl]-methyl}-4"-methyl-1,1',1"-triphenylmethane;

4,4'-bis{[3,7,11-triaza-dicyclo[11.3.1]heptadecan-1(16),13(17),14-trien-7-yl]-methyl}-4"-bromo-1,1',1"-triphenylmethane;

4,4'-bis{[3,7,11-triaza-dicyclo[11.3.1]heptadecan-1(16),13(17),14-trien-7-yl]-methyl}-4"-fluoro-1,1',1"-triphenylmethane;

4,4'-bis{[3,7,11-triaza-dicyclo[11.3.1]heptadecan-1(16),13(17),14-trien-7-yl]-methyl}-3"-chloro-1,1',1"-triphenylmethane;

4,4'-bis{[3,7,11,17-tetraaza-dicyclo[11.3.1]heptadecan-1(16),13(17),14-trien-7-yl]-methyl}-1,1',1"-triphenylmethane;

4,4'-bis{[3,7,11,17-tetraaza-dicyclo[11.3.1]heptadecan-1(16),13(17),14-trien-7-yl]-methyl}-4"-methyl-1,1',1"-triphenylmethane;

4,4'-bis{[3,7,11,17-tetraaza-dicyclo[11.3.1]heptadecan-1(16),13(17),14-trien-7-yl]-methyl}-4"-bromo-1,1',1"-triphenylmethane;

4,4'-bis{[3,7,11,17-tetraaza-dicyclo[11.3.1]heptadecan-1(16),13(17),14-trien-7-yl]-methyl}-4"-fluoro-1,1',1"-triphenylmethane;

4,4'-bis{[3,7,11,17-tetraaza-dicyclo[11.3.1]heptadecan-1(16),13(17),14-trien-7-yl]-methyl}-3"-chloro-1,1',1"-triphenylmethane.

According to the invention, the pharmaceutically acceptable salts of the compound of formula I include but are not limited to the salts formed by a compound of formula I with an acid selected from: hydrochloric acid, hydrobromic acid, sulfuric acid, phosphoric acid, nitric acid, perchloric acid, fumaric acid, acetic acid, propanoic acid, succinic acid, glycollic acid, formic acid, lactic acid, maleic acid, tartaric acid, citric acid, embonic acid, malonic acid, hydroxymaleic acid, phenylacetic acid, glutamic acid, benzoic acid, salicylic acid, fumaric acid, toluene sulfonic acid, methanesulfonic acid, naphthalene-2-sulfonic acid, benzenesulfonic acid, hydroxyl-naphthoic acid, hydroiodic acid, malic acid, tannic acid and the like. Other acids, such as oxalic acid, although they are not pharmaceutically acceptable per se, they can be used for the preparation of salts as intermediates to obtain the compounds of the invention or pharmaceutically acceptable salts thereof.

According to the invention, preferred pharmaceutically acceptable salts of formula I and/or hydrates thereof include:

3,3'-bis[(1,4,8,11-tetraazacyclotetradecan-1-yl)-methyl]-1,1',1"-triphenylmethane octahydrobromide dihydrate;

3,3'-bis[(1,4,8,11-tetraazacyclotetradecan-1-yl)-methyl]-4"-methyl-1,1',1"-triphenylmethane octahydrobromide dihydrate;

3,3'-bis[(1,4,8,11-tetraazacyclotetradecan-1-yl)-methyl]-4"-bromo-1,1',1"-triphenylmethane octahydrobromide dihydrate;

3,3'-bis[(1,4,8,11-tetraazacyclotetradecan-1-yl)-methyl]-4"-fluoro-1,1',1"-triphenylmethane octahydrobromide dihydrate;

3,3'-bis[(1,4,8,11-tetraazacyclotetradecan-1-yl)-methyl]-3"-chloro-1,1',1"-triphenylmethane octahydrobromide dihydrate;

2-{[3,3'-bis[(1,4,8,1,1-tetraazacyclotetradecan-1-yl)-methyl]-1,1'yl]-diphenyl}methylene pyridine octahydrobromide dihydrate;

4,4'-bis[(1,4,8,11-tetraazacyclotetradecan-1-yl)-methyl]-1,1',1"-triphenylmethane octahydrobromide dihydrate;

4,4'-bis[(1,4,8,11-tetraazacyclotetradecan-1-yl)-methyl]-4"-methyl-1,1',1"-triphenylmethane octahydrobromide dihydrate;

4,4'-bis[(1,4,8,11-tetraazacyclotetradecan-1-yl)-methyl]-4"-bromo-1,1',1"-triphenylmethane octahydrobromide dihydrate;

4,4'-bis[(1,4,8,11-tetraazacyclotetradecan-1-yl)-methyl]-4"-fluoro-1,1',1"-triphenylmethane octahydrobromide dihydrate;

4,4'-bis[(1,4,8,11-tetraazacyclotetradecan-1-yl)-methyl]-3"-chloro-1,1',1"-triphenylmethane octahydrobromide dihydrate;

3,3'-bis[(1,4,7,10-tetraazacyclododecan-1-yl)-methyl]-1,1',1"-triphenylmethane octahydrochloride;

3,3'-bis{[3,7,11-triaza-dicyclo[11.3.1]heptadecan-1(16),13(17),14-trien-7-yl]-methyl}-1,1',1"-triphenylmethane hexahydrobromide dihydrate;

3,3'-bis{[3,7,11-triaza-dicyclo[11.3.1]heptadecan-1(16),13(17),14-trien-7-yl]-methyl}-4"-methyl-1,1',1"-triphenylmethane hexahydrobromide dihydrate;

3,3'-bis{[3,7,11-triaza-dicyclo[11.3.1]heptadecan-1(16),13(17),14-trien-7-yl]-methyl}-4"-bromo-1,1',1"-triphenylmethane hexahydrobromide dihydrate;

3,3'-bis{[3,7,11-triaza-dicyclo[11.3.1]heptadecan-1(16),13(17),14-trien-7-yl]-methyl}-4''-fluoro-1,1',1''-triphenyl-methane hexahydrobromide dihydrate;
3,3'-bis{[3,7,11-triaza-dicyclo[11.3.1]heptadecan-1(16),13(17),14-trien-7-yl]-methyl}-3''-chloro-1,1',1''-triphenyl-methane hexahydrobromide dihydrate;
2-{[3,3'-bis((3,7,11-triaza-dicyclo[11.3.1]heptadecan-1(16),13(17),14-trien-7-yl)-methyl)-1,1'yl]-diphenyl}methylene pyridine hexahydrobromide dihydrate;
3,3'-bis{[3,7,11,17-tetraaza-dicyclo[11.3.1]heptadecan-1(16),13(17),14-trien-7-yl]-methyl}-1,1',1''-triphenyl-methane hexahydrobromide dihydrate;
3,3'-bis{[3,7,11,17-tetraaza-dicyclo[11.3.1]heptadecan-1(16),13(17),14-trien-7-yl]-methyl}-4''-methyl-1,1',1''-triphenylmethane hexahydrobromide dihydrate;
3,3'-bis{[3,7,11,17-tetraaza-dicyclo[11.3.1]heptadecan-1(16),13(17),14-trien-7-yl]-methyl}-4''-bromo-1,1',1''-triphenylmethane hexahydrobromide dihydrate;
3,3'-bis{[3,7,11,17-tetraaza-dicyclo[11.3.1]heptadecan-1(16),13(17),14-trien-7-yl]-methyl}-4''-fluoro-1,1',1''-triphenylmethane hexahydrobromide dihydrate;
3,3'-bis{[3,7,11,17-tetraaza-dicyclo[11.3.1]heptadecan-1(16),13(17),14-trien-7-yl]-methyl}-3''-chloro-1,1',1''-triphenylmethane hexahydrobromide dihydrate;
2-{[3,3'-bis((3,7,11,17-tetraaza-dicyclo[11.3.1]heptadecan-1(16),13(17),14-trien-7-yl)-methyl)-1,1'yl]-diphenyl}methylene pyridine hexahydrobromide dihydrate;
4,4'-bis{[3,7,11-triaza-dicyclo[11.3.1]heptadecan-1(16),13(17),14-trien-7-yl]-methyl}-1,1',1''-triphenylmethane hexahydrobromide dihydrate;
4,4'-bis{[3,7,11-triaza-dicyclo[11.3.1]heptadecan-1(16),13(17),14-trien-7-yl]-methyl}-4''-methyl-1,1',1''-triphenyl-methane hexahydrobromide dihydrate;
4,4'-bis{[3,7,11-triaza-dicyclo[11.3.1]heptadecan-1(16),13(17),14-trien-7-yl]-methyl}-4''-bromo-1,1',1''-triphenyl-methane hexahydrobromide dihydrate;
4,4'-bis{[3,7,11-triaza-dicyclo[11.3.1]heptadecan-1(16),13(17),14-trien-7-yl]-methyl}-4''-fluoro-1,1',1''-triphenyl-methane hexahydrobromide dihydrate;
4,4'-bis{[3,7,11-triaza-dicyclo[11.3.1]heptadecan-1(16),13(17),14-trien-7-yl]-methyl}-3''-chloro-1,1',1''-triphenyl-methane hexahydrobromide dihydrate;
4,4'-bis{[3,7,11,17-tetraaza-dicyclo[11.3.1]heptadecan-1(16),13(17),14-trien-7-yl]-methyl}-1,1',1''-triphenyl-methane; hexahydrobromide dihydrate
4,4'-bis{[3,7,11,17-tetraaza-dicyclo[11.3.1]heptadecan-1(16),13(17),14-trien-7-yl]-methyl}-4''-methyl-1,1',1''-triphenylmethane hexahydrobromide dihydrate;
4,4'-bis{[3,7,11,17-tetraaza-dicyclo[11.3.1]heptadecan-1(16),13(17),14-trien-7-yl]-methyl}-4''-bromo-1,1',1''-triphenylmethane hexahydrobromide dihydrate;
4,4'-bis{[3,7,11,17-tetraaza-dicyclo[11.3.1]heptadecan-1(16),13(17),14-trien-7-yl]-methyl}-4''-fluoro-1,1',1''-triphenylmethane hexahydrobromide dihydrate;
4,4'-bis{[3,7,11,17-tetraaza-dicyclo[11.3.1]heptadecan-1(16),13(17),14-trien-7-yl]-methyl}-3''-chloro-1,1',1''-triphenylmethane hexahydrobromide dihydrate.

According to the invention, the compounds of formula II and/or III or pharmaceutically acceptable salts or solvates thereof can be prepared by following methods, which methods comprises the steps of:

1) protecting the aldehyde group of the starting material o-bromobenzaldehyde to form a compound of formula 1; reacting the compound of formula 1 with a metallorganic reagent to achieve halogen-alkali metal exchange, and adding methyl arylformate to form a compound of formula 2;

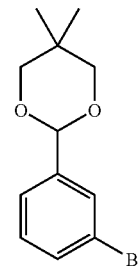

1

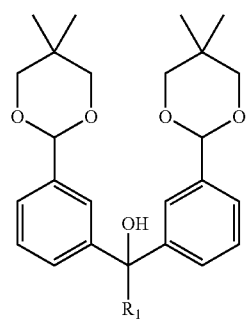

2 wherein, $R_1$ is as defined in formula I;

2) deprotecting the compound of formula 2 obtained from the step 1) with an acid, reducing the deprotected compound with a reducer, and bromating to give a compound of formula 5;

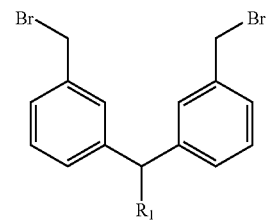

5 wherein, $R_1$ is as defined in formula I, a compound of formula 6 is obtained through the paths of the steps 1) and 2), with the exception of the starting material o-bromobenzaldehyde in the step 1) being substituted with p-bromobenzaldehyde;

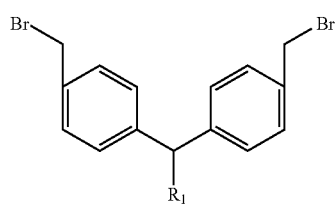

6

3)
a. reacting the starting material, i.e. a compound of formula 7 with p-tosyl radical, and cyclizing with 1,2-di-p-tosyloxypropane, deprotecting under acidic condition, and then protecting amino with p-tosyl or trifluoroacetyl radical to obtain a compound of formula 11;

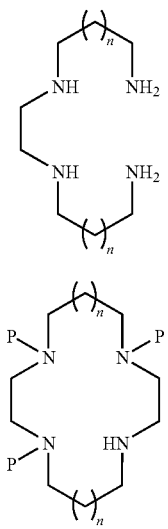

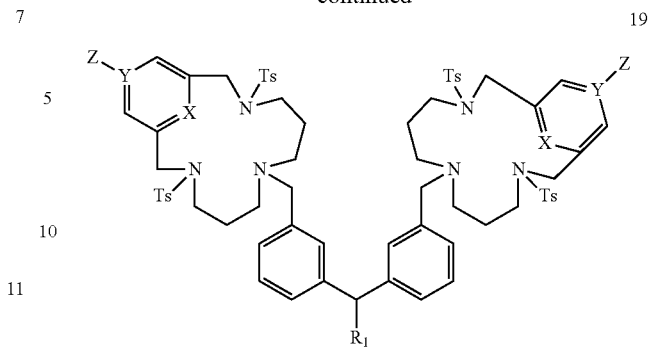

wherein, n is 0 or 1, P is p-tosyl or trifluoroacetyl radical;

b. protecting the starting material, i.e. a compound of formula 12 with diethoxyphosphoryl radical, hydrogenating, protecting amino with p-tosyl radical, and cyclizing with 1,3-dibromomethyl arene, and removing the protective group diethoxyphosphoryl radical to obtain a compound of formula 17;

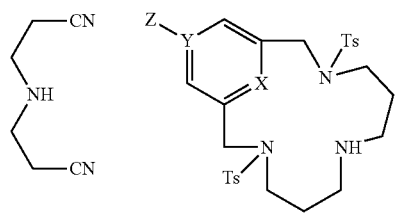

wherein, X and Y are each independently carbon atom or oxygen atom, Z=H, Cl, Ph, and the like;

4) reacting the compound of formula 5 with the compound of formula 11 (or the compound of formula 17) in the presence of anhydrous $K_2CO_3$ in acetonitrile solvent to obtain a compound of formula 18 (or a compound of formula 19);

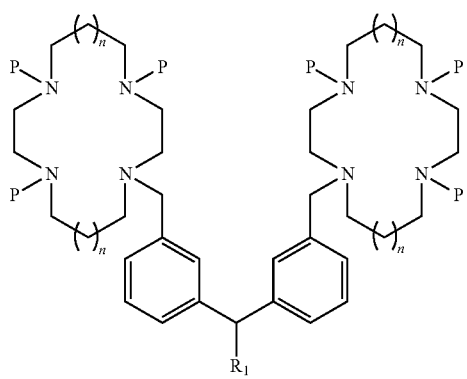

wherein, $R_1$ is as defined in formula I, P is p-tosyl or trifluoroacetyl radical; X and Y are each independently carbon atom or nitrogen atom, Z=H, Cl, Ph, and the like;

5) when P is p-tosyl radical, deprotecting the compound of formula 18 (or the compound of formula 19) under acidic condition to form a salt; or when P is trifluoroacetyl radical, deprotecting the compound of formula 18 under basic condition, and then forming a salt with an inorganic acid, thereby obtaining an inorganic acid salt of the compound of formula II;

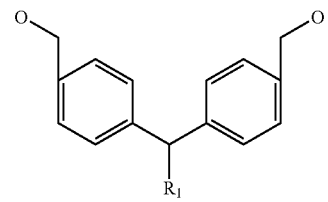

wherein, $R_1$ is as defined in formula I, 0 is as defined in formula I;

an inorganic acid salt of a compound of formula III can be obtained through above steps, with the exception of the starting material o-bromobenzaldehyde in the step 1) being substituted with p-bromobenzaldehyde;

III wherein, $R_1$ is as defined in formula I, 0 is as defined in formula I;

the synthetic reaction scheme of the compounds of formula II and III is described as follows:

step 1:

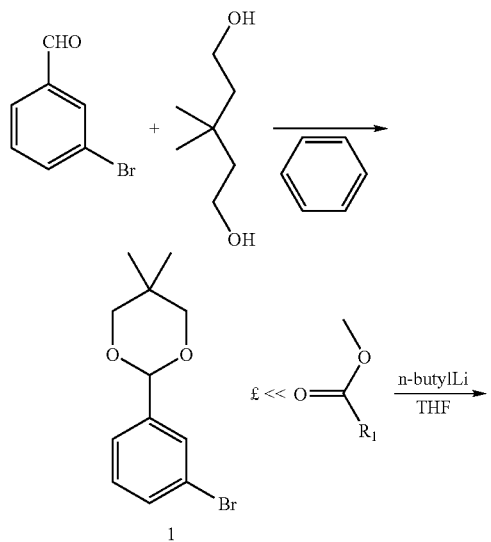

step 2:

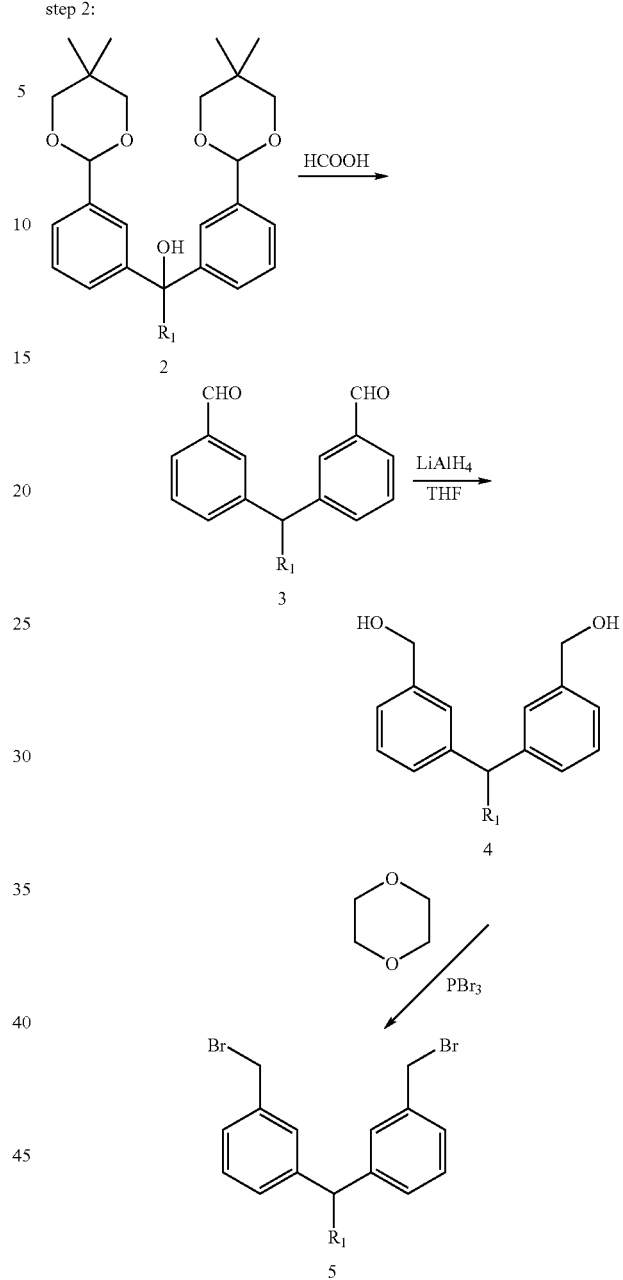

wherein, $R_1$ is as defined in formula I;

in the step 1, a solution consisting of o-bromobenzaldehyde, neopentyl glycol, pyridyl p-tolylsulfonate and benzene is refluxed and azeotropic dewatered for 3-12 hours. The reaction mixture is cooled and diluted with water. The aqueous phase is extracted with ethyl acetate. The combined organic phase is washed with saturated sodium chloride aqueous solution, dried ($Na_2SO_4$), filtrated, concentrated and column separated (eluant: n-hexane/ethyl acetate system) to give a white solid compound of formula 1. The solution of the compound of formula 1 in dried tetrahydrofuran is cooled to $-78°$ C. To the cooled solution is dropwise added n-hexane solution of n-butyl lithium, after 15 minutes, dropwise added methyl arylformate solution in dried tetrahydrofuran. The mixture is stirred at $-78°$ C. for 15-60 minutes and at $0°$ C. for 3-12 hours, and then the reaction is terminated with $NH_4Cl$. To the resultant is added ethyl acetate. The organic phase is extracted and washed with saturated sodium chloride aqueous solution, dried ($Na_2SO_4$), filtrated, concentrated and column separated (eluant: n-hexane/ethyl acetate system) to give a white solid compound of formula 2;

wherein, $R_1$ is as defined in formula I;

in this step, the compound of formula 2 is dissolved with formic acid, heat refluxed for 10-20 hours, cooled to room temperature, and concentrated in vacuum. The trace formic acid is neutralized with saturated $NaHCO_3$. The aqueous phase is extracted with ethyl acetate. The combined organic phase is washed with saturated sodium chloride aqueous solution, dried ($Na_2SO_4$), filtrated, concentrated and column separated (eluant: n-hexane/ethyl acetate system) to give a white solid compound of formula 3. To the compound of formula 3 in dried tetrahydrofuran solution is dropwise added dried tetrahydrofuran suspension of aluminum lithium hydride at a temperature of $0°$ C. The mixture is allowed to react at room temperature for 1-10 hours. To the system is added saturated $NH_4Cl$. The resultant is filtrated, concentrated and column separated (eluant: n-hexane/ethyl acetate system) to give a white solid intermediate of formula 4. The compound of formula 4 is dissolved in dried dioxane. To the solution is dropwise added phosphorus tribromide. The mixture is allowed to react at room temperature over night. To the system is added a small amount of water to destroy excessive phosphorus tribromide. The resultant is concentrated and column separated (eluant: n-hexane/ethyl acetate system) to give a white solid compound of formula 5;

step 3:

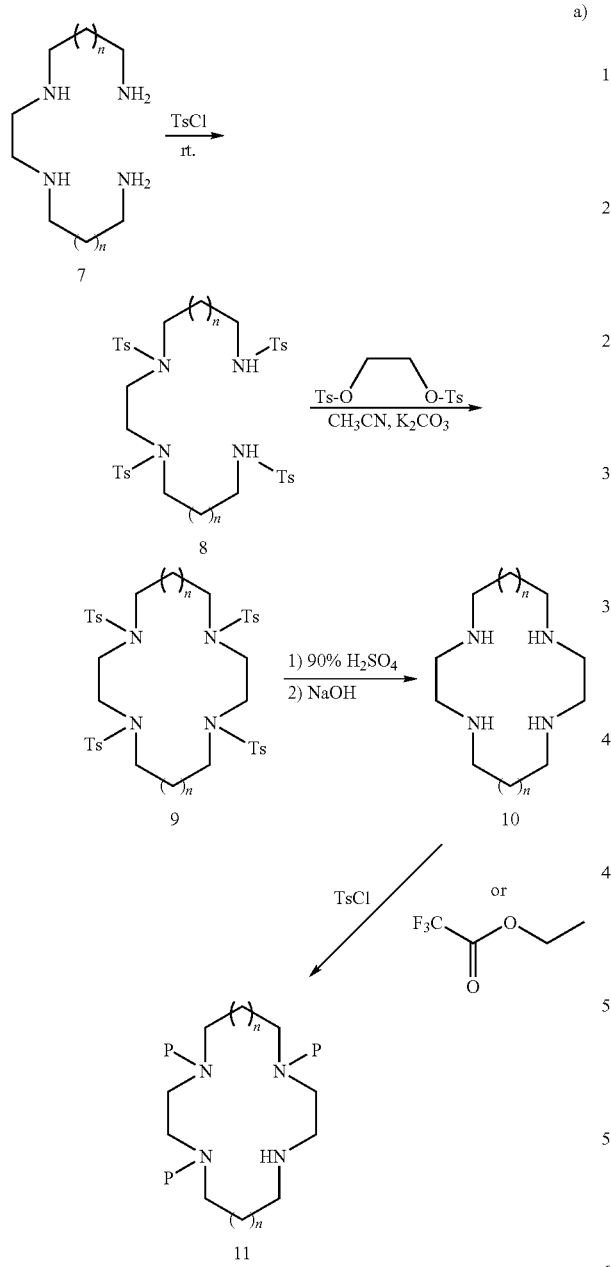

wherein, n is 0 or 1, Ts is tosyl radical, P is trifluoroacetyl or p-tosyl radical;

To the NaOH solution of the starting material 7 is dropwise added ether solution of tosyl chloride. The system is stirred over night. A white solid is formed and filtrated. The filter cake is washed with water and ethyl ether, respectively, recrystallized to give a white solid intermediate of formula 8. To the dried acetonitrile solution of the compound of formula 8 is slowly dropwise added dried acetonitrile solution of 1,2-di-p-tosyloxypropane under reflux state, refluxed for 2-4 days, stood until room temperature. A white solid is precipitated and filtrated. The filter cake is washed with water and ethyl acetate, respectively, recrystallized to give a white solid compound of formula 9. The compound of formula 9 is dissolved in 90% concentrated sulfuric acid, allowed to react at 100° C. for 24-48 hours, stood until room temperature. To the reaction solution are dropwise added successively ethanol and ethyl ether. A white solid is precipitated, filtrated, dried, and dissolved in NaOH solution. The aqueous phase is extracted with chloroform. The chloroform phase is combined, concentrated, recrystallized to give a white solid compound of formula 10. To the chloroform solution of the compound of formula 10 and triethylamine is dropwise added chloroform solution of tosyl chloride. The mixture is allowed to react at room temperature over night, concentrated and column separated (eluant: dichloromethane/methanol system) to give a white solid compound of formula 11 (protective group is tosyl); or to the methanol solution of the compound of formula 10 is dropwise added ethyl trifluoroacetate. The mixture is allowed to react at room temperature over night, concentrated and column separated (eluant: ethyl acetate) to give a white solid compound of formula 11 (protective group is trifluoroacetyl);

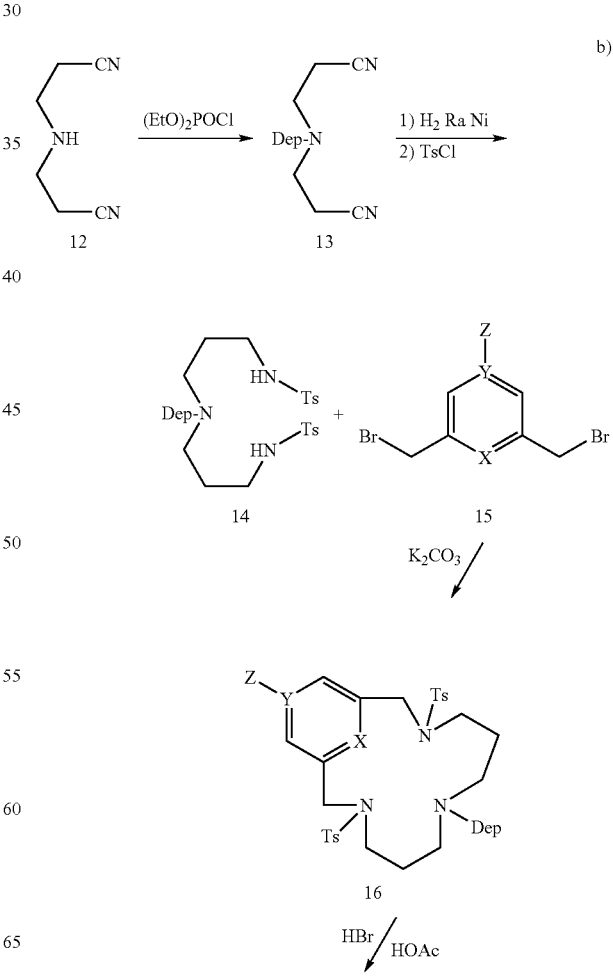

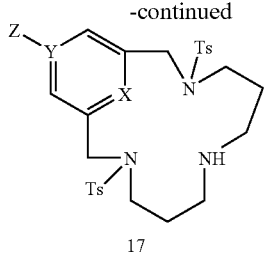

17

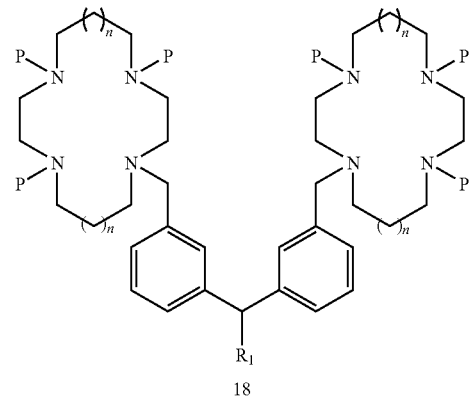

18 wherein, Dep is diethoxyphosphoryl radical, Ts is p-tosyl radical, X and Y are each independently carbon atom or nitrogen atom, Z=H, Cl, Ph, etc; The compound of the starting material 12 is dissolved in dichloromethane. To the system is added triethylamine, and then dropwise added dichloromethane solution of diethoxyphosphoryl at room temperature. The mixture is allowed to react at room temperature over night. The resultant is concentrated and performed to column chromatography (eluant: dichloromethane/methanol system) to give a colorless transparent oily compound of formula 13. The compound of formula 13 is dissolved in methanolic ammonia solution. To the system is added Raney nickel alloy as catalyst. The mixture is catalytically hydrogenated at room temperature and 45 Psi, after 48 hours, the reaction is terminated. The resultant is filtrated, concentrated, dried in vacuum, and dissolved in dichloromethane. To the solution is added triethylamine, and then dropwise added dichloromethane solution of p-tosyl chloride. The mixture is allowed to react at room temperature over night, filtrated, concentrated, column separated (eluant: dichloromethane/methanol system) to give a white solid compound of formula 14. The compound of formula 14 is dissolved in acetonitrile. To the solution is added anhydrous $K_2CO_3$. The system is refluxed for 1 hour. To the system is slowly added acetonitrile solution of a compound of formula 15. The mixture is refluxed for 24-48 hours, stood until room temperature, filtrated, concentrated, column separated (eluant: dichloromethane/methanol system) to give a white solid compound of formula 16; the compound of formula 16 is dissolved in glacial acetic acid. To the solution is added 45% glacial acetic acid solution of HBr (commercially available from Alfa). The system is stirred at room temperature for 2 hours. To the system is added a large amount of ethyl ether. A solid is precipitated and filtrated by suction to give an orange solid. The solid is dissolved in dichloromethane. The organic phase is washed with NaOH solution and saturated sodium chloride aqueous solution, respectively, dried ($Na_2SO_4$), filtrated, concentrated and column separated (eluant: dichloromethane/methanol system) to obtain a white solid compound of formula 17;

step 4:

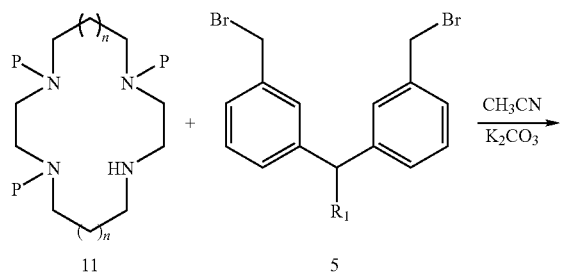

wherein n is 0 or 1, P is p-tosyl or trifluoroacetyl radical, $R_1$ is as defined in formula I;

the compound of formula II, the compound of formula 5 and anhydrous $K_2CO_3$ are refluxed in acetonitrile for 24-48 hours, allowed to react and stood until room temperature and filtrated. The filtrate is concentrated and column separated (eluant: dichloromethane/methanol system) to give a white solid compound of formula 18);

A compound of formula 19 is prepared according to the path of the step 4, with the exception of the starting material compound of formula 11 in the step 4 being substituted with the compound of formula 17;

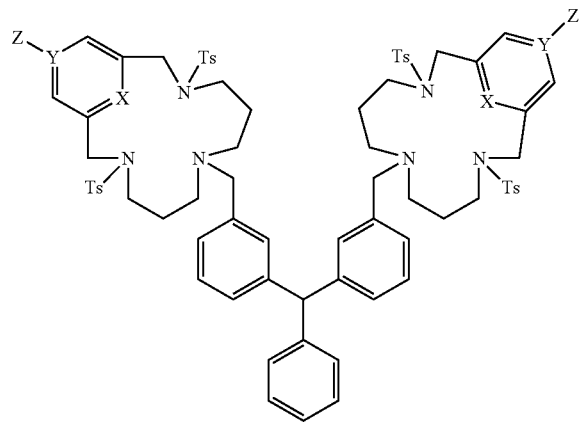

19 wherein, $R_1$ is as defined in formula I, X and Y are carbon atom or oxygen atom, Z=H, Cl, Ph, etc.;

step 5:

1)

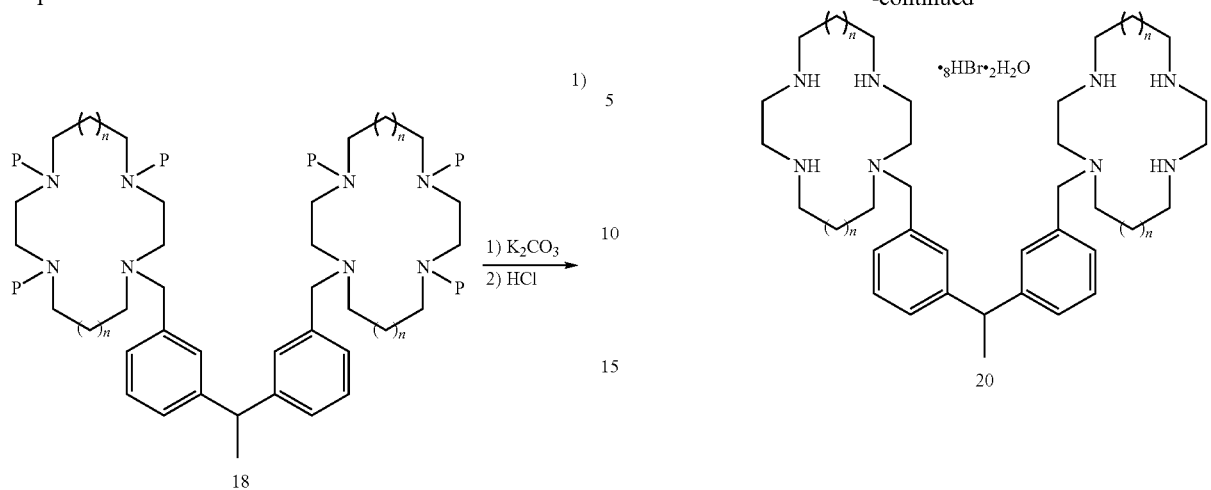

1) K₂CO₃
2) HCl

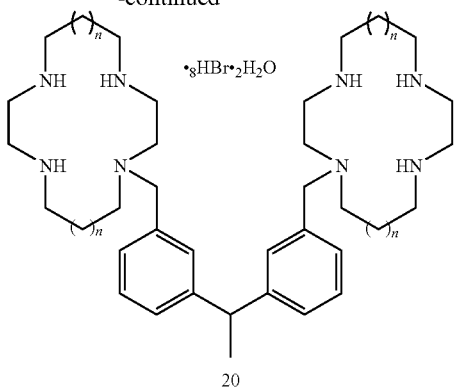

wherein, n is 0 or 1, P is trifluoroacetyl radical, R₁ is as defined in formula I;

the compound of formula 12 and anhydrous K₂CO₃ are refluxed in methanol over night. To the system is added toluene to taking out methanol (based on azeotropism principle). The mixture is stood until room temperature and filtrated. The filtrate is concentrated and dried. To the system are added a small amount of methanol and ethyl ether solution, and introduced dried HCl gas. A straw yellow solid is precipitated, filtrated to give a compound of formula 20; i.e. the hydrochloride salt of the compound of formula II;

2)

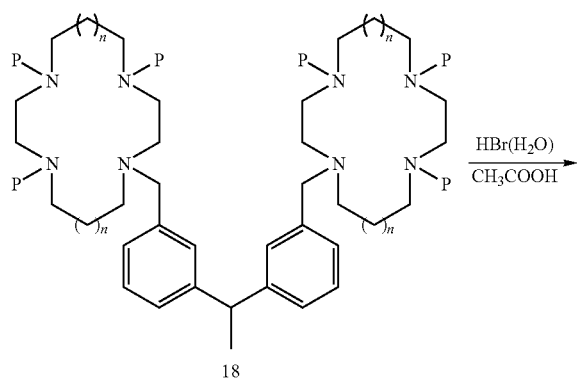

HBr(H₂O) / CH₃COOH wherein, n is 0 or 1, P is p-tosyl radical, R₁ is as defined in formula I;

the compound of formula 12 is refluxed in the mixture solution of hydrobromic acid and glacial acetic acid for 24-48 hours, stood until room temperature. To the system is added a large amount of acetone. A white solid is precipitated, filtrated, washed with acetone to give a white solid compound of formula 21; i.e. the hydrobromide salt of the compound of formula II;

a white solid compound of formula 22, i.e. the hydrobromide salt of the compound of formula II are prepared through the path of the step 4 only the starting material compound of formula 12 in the step 5 is substituted with the compound 22 of formula;

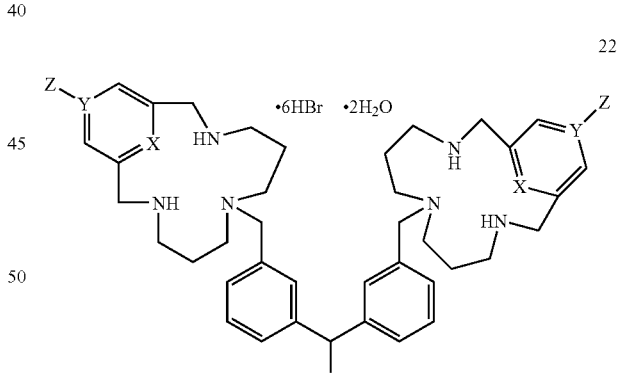

wherein, R₁ is as defined in formula I, X and Y are each independently carbon atom or oxygen atom, Z=H, Cl, Ph, etc.;

further, compounds 23, 24 and 25 i.e. hydrochloride or hydrobromide salts of the compound of formula III are prepared, respectively through above steps only the starting material o-bromobenzaldehyde in the step 1 is substituted with p-bromobenzaldehyde.

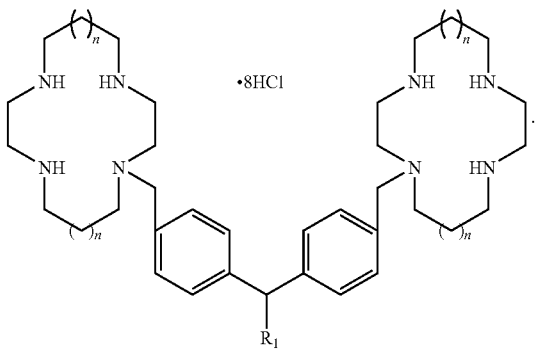

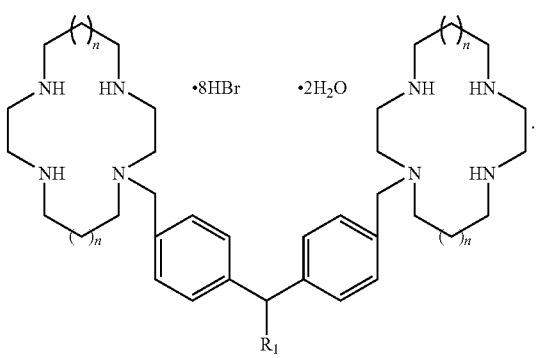

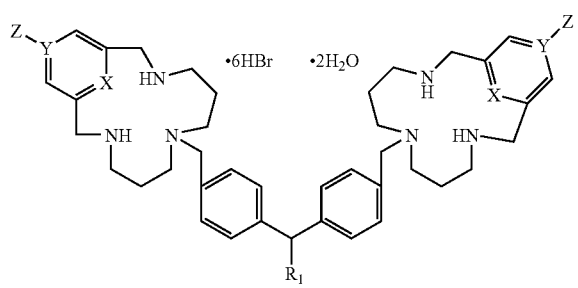

wherein, $R_1$ is as defined in formula I, X and Y are each independently carbon atom or oxygen atom, Z=H, Cl, Ph, etc.

Those skilled in the art should be conscious of that the compounds of the invention can be used in the form of pharmaceutically acceptable salts or solvates thereof. Pharmaceutically acceptable salts of the compound of formula I include conventional salts formed with pharmaceutically acceptable inorganic acids or organic acids or inorganic bases or organic bases, and acid addition salts of quaternary ammonium.

The invention also includes the prodrugs of the compounds according to the invention, once the prodrugs are administered, they are performed to chemical conversions through metabolism course, and then changed into drugs having activity. Generally, these prodrugs are functional derivatives of the compounds of the invention, which are easily converted in vivo into desired compounds of formula (I). For example, "Design of Prodrugs", edited by H Bund Saard, Elsevier, 1985 described conventional methods to select and prepare suitable prodrugs derivatives.

The invention further includes active metabolites of the compounds of the invention.

The pharmaceutical composition of the invention includes an effective dosage of the compound of formula I according to the invention or a pharmaceutically acceptable salt or a hydrate thereof and one or more suitable pharmaceutically acceptable carriers. The pharmaceutical composition can be used for in vivo treatment and exhibits biocompatibility. Said pharmaceutical composition can be prepared into various dosage forms based on the requirements of different administration paths.

The pharmaceutically acceptable carriers include but are not limited to: ion exchangers, alumina, aluminum stearate, lecithin, serum protein such as human serum albumin, buffers such as phosphates, glycerin, sorbic acid, potassium sorbate, part of glyceride mixtures of saturated vegetable fatty acids, water, salts or electrolytes, such as protamine, disodium hydrogen phosphate, potassium hydrogen phosphate, sodium chloride, zinc salts, colloided silica, magnesium trisilicate, polyvinylpyrrolidone, cellulose materials, polyethylene glycol, carboxymethylcellulose sodium, polyacrylates, beeswax, lanolin.

The pharmaceutical compositions of the compounds according to the invention can be administered in any manner described below: oral administration, aerosol, rectal application, nasal application, buccal application, local application, non-intestinal application, such as subcutaneous, vein, muscle, intraperitoneal, intrathecal, intraventricular, intrasternal or intracal injection or importation, or by means of external reservoir, in which intravenous injection administration is preferred.

The compounds of the invention can be administered in sterile injection formulation form, including sterile injection aqueous or oil suspension or sterile injection solution, in which spendable carriers and solvents include water, Ringer's solution and isosmotic sodium chloride solution. Additionally, sterile non-volatile oils can also be used as solvents or suspension media, such as monoglyceride or diglyceride.

Besides, it should be pointed out that the use dosage and use method of the compounds of the invention depend on many factors, including the age, body weight, sex, natural health status and nutritional status of patients, the activity intensity, administration time and metabolism rate of the compounds, the severity degree of disorders and the subjective judgment of physician. The preferred use dosage is between 0.01 and 100 mg per kilogram body weight per day, in which the most preferred dosage is between 5 and 10 mg per kilogram body weight per day.

EMBODIMENTS

Following examples will further describe the invention, however, these examples do not constitute a limitation to the invention in any way.

$^1$H-NMR spectrum of the compounds is measured by means of Bruker ARX 400 NMR spectrometer. FAB mass spectrum of the compounds is measured by means of Zabspect fine resolution magnetic mass spectrometer.

EXAMPLES

Example 1

Preparation of 3,3'-bis[(1,4,8,11-tetraazacyclotetradecan-1-yl)-methyl]-1,1',1"-triphenylmethane octahydrobromide dihydrate

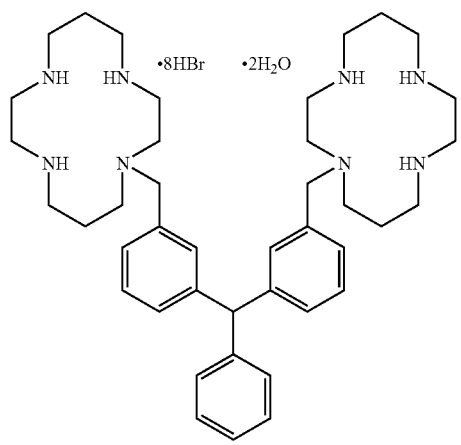 [SMILES: c1ccc(C(c2cccc(CN3CCCNCCNCCCNCC3)c2)c2cccc(CN3CCCNCCNCCCNCC3)c2)cc1 ; "·8HBr" ; "·2H2O"]

a. 2-(3-Bromo-phenyl)-5,5-dimethyl-1,3-dioxane

A solution consisting of o-bromobenzaldehyde (150 mmol), neopentyl glycol (180 mmol), pyridyl p-tolylsulfonate (15 mmol) and benzene (800 ml) was refluxed and azeotropic dewatered for 6 hours. The reaction mixture was cooled and diluted with water. The aqueous phase was extracted with ethyl acetate. The combined organic phase was washed with saturated sodium chloride aqueous solution, dried ($Na_2SO_4$), filtrated, concentrated and column separated (eluant: n-hexane/ethyl acetate system) to give 35.1 g of a white solid ketal, yield 86%.

b. Bis[3-(5,5'-dimethyl-[1,3]-dioxan-2-yl)-phenyl]-phenyl-methanol

The solution of solid ketal (20 mmol) obtained from the step a in dried tetrahydrofuran (50 ml) was cooled to −78° C. To the cooled solution was dropwise added n-hexane solution of n-butyl lithium (7 ml, 2.88 mol/L, commercially available from ACROS), after 15 minutes, dropwise added methyl benzoate (8 mmol) solution in dried tetrahydrofuran (15 ml). The mixture was stirred at −78° C. for 15 minutes and at 0° C. for 3 hours, and then the reaction was terminated with 10% $NH_4Cl$ (40 ml). To the resultant was added ethyl acetate (40 ml). The organic phase was extracted and washed with saturated sodium chloride aqueous solution, dried ($Na_2SO_4$), filtrated, concentrated and column separated (eluant: n-hexane/ethyl acetate system) to give 2.6 g of a white solid, yield 67%.

c. 3,3'-(Phenyl)methylenedibenzaldehyde

The triaryl methanol derivative (10 mmol) prepared by the method as described in step b was dissolved in formic acid (50 ml), heat refluxed over night, cooled to room temperature, and concentrated in vacuum. The trace formic acid was neutralized with saturated $NaHCO_3$. The aqueous phase was extracted with ethyl acetate. The combined organic phase was washed with saturated sodium chloride aqueous solution, dried ($Na_2SO_4$), filtrated, concentrated and column separated (eluant: n-hexane/ethyl acetate system) to give 1.8 g of an oil substance, yield 60%.

d. 3,3'-(Aryl)methylenedibenzohydrol

To the dried tetrahydrofuran (50 ml) solution of the deprotected aldehyde (5 mmol) prepared by the method as described in the step c was dropwise added dried tetrahydrofuran (10 ml) suspension of aluminum lithium hydride (20 mmol) at a temperature of 0° C., allowed to react at room temperature for 1 hour, added a small amount of saturated $NH_4Cl$, filtrated, concentrated and column separated (eluant: n-hexane/ethyl acetate system) to give 1.2 g of a white solid, yield 80%.

e. 3,3'-(Phenyl)methylenedibenzyl bromide

The alcohol (2 mmol) obtained from the step d was dissolved in dried dioxane (30 ml). To the solution was dropwise added phosphorus tribromide (8 mmol). The mixture was allowed to react at room temperature over night. To the resultant was added a small amount of water to destroy excessive phosphorus tribromide. The resultant was concentrated and column separated (eluant: n-hexane/ethyl acetate system) to give 0.56 g of a colorless oil substance, yield 65%, MS[M]+=430.2 m/e.

f. N,N',N",N'''-tetra-p-tosyldi(3-aminopropyl)-ethyldiamine

Di(3-aminopropyl)-ethyldiamine (30 mmol) was dissolved in NaOH aqueous solution (10%, 50 ml). To the system was slowly dropwise added ether solution (100 ml) of tosyl chloride (130 mmol) at 0° C., the adding was completed after 2 hours. The mixture was allowed to react with stir at room temperature over night. The resultant suspension was filtrated. The filter cake was washed with water and ethyl ether, respectively, dried in vacuum to give 19.2 g of a white solid, yield 80%.

g. 1,4,8,11-Tetra-p-tosyl-1,4,8,11-tetraazacyclotetradecane

The p-tosyl protected amine (10 mmol) obtained from the step f, anhydrous potassium carbonate (100 mmol) and anhydrous acetonitrile (200 ml) were heat refluxed with stir for 1 h. To the system was very slowly dropwise added anhydrous acetonitrile solution of 1,2-di-p-tosyloxyethane (10 mmol). Upon the completion of the dropwise adding in 24 hours, the mixture was heat refluxed for 48 hours, and the system was stood until room temperature. The resultant suspension was filtrated. The filter cake was washed with water and ethyl acetate, respectively, dried in vacuum to give 5.1 g of a white solid 1,4,8,11-tetra-p-tosyl-1,4,8,11-tetraazacyclotetradecane, yield 62.5%.

h. 1,4,8,11-Tetraazacyclotetradecane 1,4,8,11-Tetra-p-tosyl-1,4,8,11-tetraazacyclotetradecane (13 mmol) was dissolved in 90% concentrated sulfuric acid, allowed to react with stir at 100° C. for 48 hours, and cooled to 0° C. To the resultant was dropwise added anhydrous ethanol (120 ml) and anhydrous ethyl ether (100 ml) successively. A solid was precipitated and filtrated. The filter cake was washed with a small amount of anhydrous ethanol and anhydrous ethyl ether, dried in vacuum. The resultant off white solid was dissolved with NaOH aqueous solution (90 ml, 1 mol/L), and extracted with chloroform (3×100 ml). The chloroform layer was dried over anhydrous sodium sulfate over night, reduced pressure distilled off chloroform, dried in vacuum to give a white solid product, recrystallized with toluene to obtain 2.2 g of 1,4,8,11-tetraazacyclotetradecane, yield 85%, MS[M]+=200.3 m/e, $^1$H-NMP (400 M HZ, CDCl$_3$) δppm: 1.72 (t, 4H), 2.23 (s, 4H), 2.68 (s, 8H), 2.75 (t, 8H).

i. 1,4,8-Tri(p-tosyl)-1,4,8,11-tetraazacyclotetradecane

The azacrown ether (21 mmol) obtained from the step h was dissolved in dichloromethane (150 ml). To the system was added triethylamine (18 ml), and then dropwise added at room temperature p-tosyl chloride (43 mmol) in 300 ml dichloromethane solution. Upon the completion of dropwise addition, the mixture was stirred at room temperature over night. To the system was added water (40 ml). The organic phase was separated, dried over anhydrous sodium sulfate over night, reduced pressure distilled off dichloromethane, recrystallized with methanol to obtain 6.0 g of a first solid; the mother liquor was distilled under reduced pressure and recrystallized, the resultant oily substance was dissolved with dicholormethane (100 ml) and triethylamine (10 ml). To this system was dropwise added p-tosyla chloride (2.0 g, 10 mmol) in dicholormethane (50 ml) solution. The mixture was allowed to react at room temperature for 2 hours, reduced pressure distilled off dichloromethane, recrystallized with methanol to obtain 2.6 g of a second batch of solid. The two solids were combined to provide 8.6 g of 1,4,8-tri(p-tosyl)-1,4,8,11-tetraazacyclotetradecane, yield 62%, MS[M]+=662.0 m/e.

j. 3,3'-Bis {[1,4,8-tri(p-tosyl)-1,4,8,11-tetraazacyclotetradecan-1-yl]methyl}-1,1',1''-triphenylmethane The intermediate (1 mmol) obtained from the step e, 3,3'-(phenyl)methylenedibenzyl bromide (2 mmol) obtained from the step i, anhydrous potassium carbonate (3 mmol) and dried acetonitrile (20 ml) were heat refluxed with intensive stir for 24 hours, stood, filtrated. The filtrate was concentrated and column separated (eluant: dichloromethane/methanol system) to obtain 1.2 g of a white foamy solid, yield 75%, MS[M]+=1594.2 m/e.

k. Deprotection with a Mixed Acid

The intermediate (0.3 mmol) obtained from the step j was refluxed for 48 hours in a mixed solution of hydrobromic acid and glacial acetic acid (volume ratio: 2/3, 10 ml). The reactant was stood until room temperature. To the resultant was added a great deal of acetone. A white solid was precipitated, filtrated, washed with acetone to obtain 0.22 g of title compound, straw yellow solid, yield 54%.

$^1$H-NMR (400 MHz, D$_2$O) δppm: 1.93-2.02 (br m, 8H), 3.05-3.50 (br m, 32H), 4.13 (s, 4H), 5.68 (s, 1H), 7.17-7.33 (m, 13H); FAB-MS (m/z): 669.2 [M+H]$^+$.

Example 2

Preparation of 3,3'-bis[(1,4,8,11-tetraazacyclotetradecan-1-yl)-methyl]-4'''-methyl-1,1',1'''-triphenyl-methane octahydrobromide dihydrate

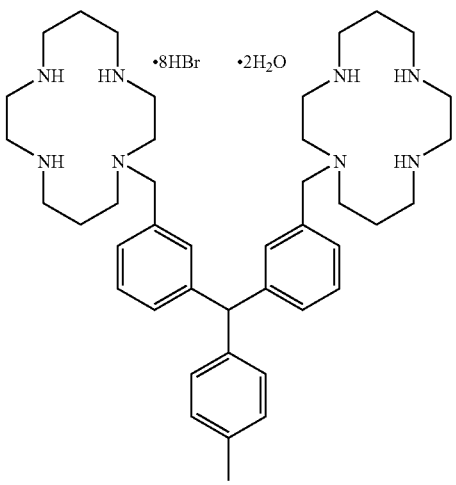 [SMILES: Cc1ccc(C(c2cccc(CN3CCCNCCNCCCNCC3)c2)c2cccc(CN3CCCNCCNCCCNCC3)c2)cc1 ; "·8HBr" ; "·2H2O"]

a. 3,3'-(4-Methyl-phenyl)methylenedibenzyl bromide

A colorless oily substance was obtained by the method for preparing 3,3'-(phenyl)methyldibenzyl bromide in Example 1, with the exception of methyl benzoate in the step b of Example 1 being substituted by methyl-p-methylbenzoate, MS[M]+=430.2 m/e.

b. 3,3'-Bis {[1,4,8-tri(p-tosyl)-1,4,8,11-tetraazacyclotetradecan-1-yl]-m ethyl}-4'''-methyl-1,1',1'''-triphenylmethane A white foamy solid was obtained by the method for preparing 3,3'-bis{[1,4,8-tri(p-tosyl)-1,4,8,11-tetraazacyclotetradecan-1-yl]-methyl}-1,1',1'''-triphenylmethane in the step g of Example 1, with the exception of 3,3'-(phenyl)methylenedibenzyl bromide in the step g of Example 1 being substituted by 3,3'-(4-methyl-phenyl)methylenedibenzyl bromide obtained in the step a above, MS[M]+=1608.2 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 2.14-2.26 (br m, 8H), 2.52 (s, 3H), 3.28-3.52 (br m, 32H), 4.24 (s, 4H), 5.93 (s, 1H), 7.36-7.66 (m, 12H); FAB-MS (m/z): 683.3 [M+H]$^+$.

Example 3

Preparation of 3,3'-bis[(1,4,8,11-tetraazacyclotetradecan-1-yl)-methyl]-4''-bromo-1,1',1''-triphenylmethane octahydrobromide dihydrate

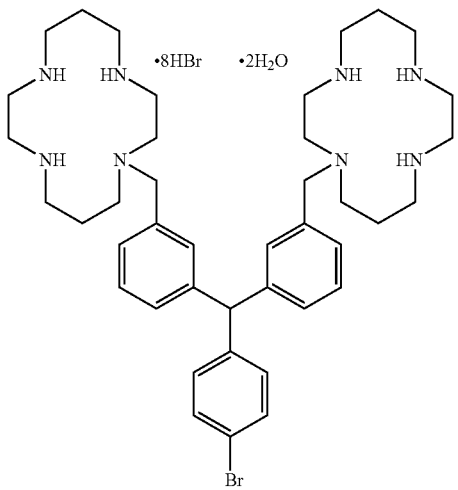 [SMILES: Brc1ccc(C(c2cccc(CN3CCCNCCNCCCNCC3)c2)c2cccc(CN3CCCNCCNCCCNCC3)c2)cc1 ; "·8HBr" ; "·2H2O"]

a. 3,3'-(4-Bromo-phenyl)methylenedibenzyl bromide

A colorless oily substance was obtained by the method for preparing 3,3'-(phenyl)methyldibenzyl bromide in Example 1, with the exception of methyl benzoate in the step b of Example 1 being substituted with methyl p-bromobenzoate, MS[M]+=509.1 m/e.

b. 3,3'-Bis {[1,4,8-tri(p-tosyl)-1,4,8,11-tetraazacyclotetradecan-1-yl]-methyl }-4''-bromo-1,1',1''-triphenylmethane A white foamy solid was obtained by the method for preparing 3,3'-bis{[1,4,8-tri(p-tosyl)-1,4,8,11-tetraazacyclotetradecan-1-yl]-methyl }-1,1',1''-triphenylmethane in the step g of Example 1, with the exception of 3,3'-(phenyl)methylenedibenzyl bromide in the step g of Example 1 being substituted with 3,3'-(4-bromo-phenyl)methylenedibenzyl bromide obtained in the step a above, MS[M]+=1673.1 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.97-1.99 (br m, 8H), 3.12-3.40 (br m, 32H), 4.19 (s, 4H), 5.69 (s, 1H), 7.19-7.37 (m, 12H); FAB-MS (m/z): 749.2 [M+H]$^+$.

Example 4

Preparation of 3,3'-bis[(1,4,8,11-tetraazacyclotetradecan-1-yl)-methyl]-4''-fluoro-1,1',1''-triphenylmethane octahydrobromide dihydrate

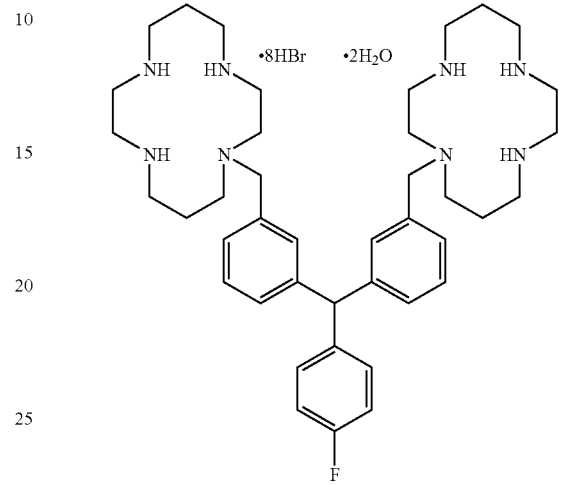

a. 3,3'-(4-Fluoro-phenyl)methylenedibenzyl bromide

A colorless oily substance was obtained by the method for preparing 3,3'-(phenyl)methyldibenzyl bromide in Example 1, with the exception of methyl benzoate in the step b of Example 1 being substituted with methyl p-fluorobenzoate, MS[M]+=448.2 m/e.

b. 3,3'-Bis{[1,4,8-tri(p-tosyl)-1,4,8,11-tetraazacyclotetradecan-1-yl]-methyl}-4''-fluoro-1,1',1''-triphenylmethane A white foamy solid was obtained by the method of preparing 3,3'-bis{[1,4,8-tri(p-tosyl)-1,4,8,11-tetraazacyclotetradecan-1-yl]-methyl }-1,1',1''-triphenylmethane in the step g of Example 1, with the exception of 3,3'-(phenyl)methylenedibenzyl bromide in the step g of Example 1 being substituted with 3,3'-(4-fluoro-phenyl)methylenedibenzyl bromide obtained in the step a above, MS[M]+=1612.2 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.91 (br, 8H), 2.99-3.26 (br m, 32H), 4.07 (s, 4H), 5.63 (s, 1H), 6.95-7.29 (m, 12H); MS[M]+=687.4 [M+H]$^+$.

Example 5

Preparation of 3,3'-bis[(1,4,8,11-tetraazacyclotetradecan-1-yl)-methyl]-3"-chloro-1,1',1"-triphenylmethane octahydrobromide dihydrate

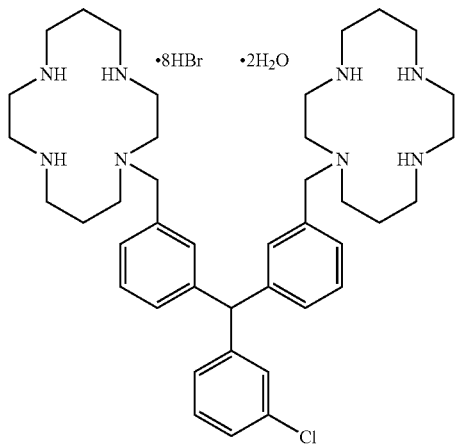 [SMILES: Clc1cccc(C(c2cccc(CN3CCCNCCNCCCNCC3)c2)c2cccc(CN3CCCNCCNCCCNCC3)c2)c1 ; "·8HBr" ; "·2H2O"]

a. 3,3'-(3-Chloro-phenyl)methylenedibenzyl bromide

A colorless oily substance was obtained by the method for preparing 3,3'-(phenyl)methyldibenzyl bromide in Example 1, with the exception of methyl benzoate in the step b of Example 1 being substituted with methyl m-chlorobenzoate, MS[M]+=509.1 m/e.

b. 3,3'-Bis{[1,4,8-tri(p-tosyl)-1,4,8,11-tetraazacyclotetradecan-1-yl]methyl}-3"-chloro-1,1',1"-triphenylmethane A white foamy solid was obtained by the method for preparing 3,3'-bis{[1,4,8-tri(p-tosyl)-1,4,8,11-tetraazacyclotetradecan-1-yl]-methyl }-1,1',1"-triphenylmethane in the step g of Example 1, with the exception of 3,3'-(phenyl)methylenedibenzyl bromide in the step g of Example 1 being substituted with 3,3'-(3-chloro-phenyl)methylenedibenzyl bromide obtained in the step a above, MS[M]+=1628.7 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.96-2.00 (br m, 8H), 3.06-3.33 (br m, 32H), 4.14 (s, 4H), 5.72 (s, 1H), 7.20-7.39 (m, 12H); FAB-MS (m/z): 703.4 [M+H]$^+$.

Example 6

Preparation of 2-{[3,3'-bis[(1,4,8,11-tetraazacyclotetradecan-1-yl)-methyl]-1,1'yl]-diphenyl}methylenepyridyl octahydrobromide dihydrate

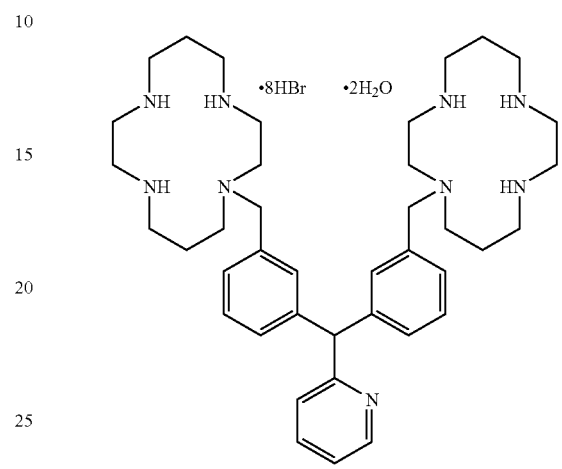

a. 3,3'-(Pyridyl-2-yl)methylenedibenzyl bromide

A colorless oily substance was obtained by the method for preparing 3,3'-(phenyl)methyldibenzyl bromide in Example 1, with the exception of methyl benzoate in the step b of Example 1 being substituted with methyl pyridyl-2-formate, MS[M]+=431.2 m/e.

b. 2-{[3,3'-Bis([1,4,8-tri(p-tosyl)-1,4,8,11-tetraazacyclotetradecan-1-yl]-methyl)-1,1'yl]-diphenyl}methylenepyridine A white foamy solid was obtained by the method of preparing 3,3'-bis{[1,4,8-tri(p-tosyl)-1,4,8,11-tetraazacyclotetradecan-1-yl]-methyl }-1,1',1"-triphenylmethane in the step g of Example 1, with the exception of 3,3'-(phenyl)methylenedibenzyl bromide in the step g of Example 1 being substituted with 3,3'-(pyrid-2-yl)methylenedibenzyl bromide obtained in the step a above, MS[M]+=1595.2 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.90-1.92 (br m, 8H), 3.11-3.30 (br m, 32H), 4.06 (s, 4H), 6.08 (s, 1H), 7.14-8.52 (m, 12H); FAB-MS (m/z): 670.4 [M+H]$^+$.

Example 7

Preparation of 4,4'-bis[(1,4,8,11-tetraazacyclotetradecan-1-yl)-methyl]-1,1',1''-triphenylmethane octahydrobromide dihydrate

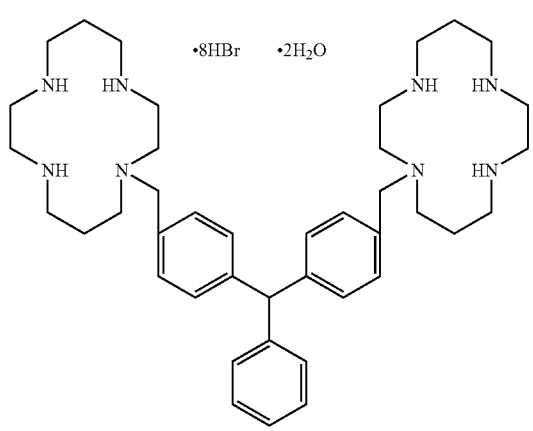 [SMILES: c1ccc(C(c2ccc(CN3CCCNCCNCCCNCC3)cc2)c2ccc(CN3CCCNCCNCCCNCC3)cc2)cc1 ; "·8HBr" ; "·2H2O"]

a. 4,4'-(phenyl)methylenedibenzyl bromide 0.56 g of a colorless oily substance was obtained by the method for preparing 3,3'-(phenyl)methyldibenzyl bromide in Example 1, with the exception of o-bromobenzaldehyde in the step a of Example 1 being substituted with p-bromobenzaldehyde, MS[M]+=430.2 m/e.

b. 4,4'-Bis {[1,4,8-tri(p-tosyl)-1,4,8,11-tetraazacyclotetradecan-1-yl]methyl}-1,1',1''-triphenylmethane A white foamy solid was obtained by the method of preparing 3,3'-bis{[1,4,8-tri(p-tosyl)-1,4,8,11-tetraazacyclotetradecan-1-yl]-methyl }-1,1',1''-triphenylmethane in the step g of Example 1, with the exception of 3,3'-(phenyl)methylenedibenzyl bromide in the step g of Example 1 being substituted with 4,4'-(phenyl)methylenedibenzyl bromide obtained in the step a above, MS[M]+=1594.1 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.87-2.00 (br m, 8H), 3.11-3.32 (br m, 32H), 4.13 (s, 4H), 5.60 (s, 1H), 7.18-7.27 (m, 13H); FAB-MS (m/z): 669.3 [M+H]$^+$.

Example 8

Preparation of 4,4'-bis[(1,4,8,11-tetraazacyclotetradecan-1-yl)-methyl]-4''-methyl-1,1',1''-triphenylmethane octahydrobromide dihydrate

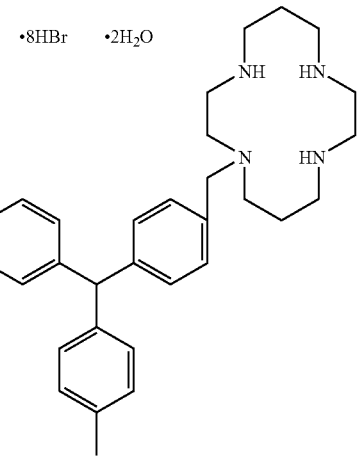

a. 4,4'-(4-Methyl-phenyl)methylenedibenzyl bromide 0.56 g of a colorless oily substance was obtained by the method for preparing 3,3'-(phenyl)methyldibenzyl bromide in Example 1, with the exception of o-bromobenzaldehyde in the step a of Example 1 being substituted with p-bromobenzaldehyde, and then of methyl benzoate in the step b of Example 1 being substituted with methyl p-methylbenzoate, MS[M]+=444.2 m/e.

b. 4,4'-Bis{[1,4,8-tri(p-tosyl)-1,4,8,11-tetraazacyclotetradecan-1-yl]-methyl}-4''-methyl-1,1',1''-triphenylmethane A white foamy solid was obtained by the method for preparing 3,3'-bis{[1,4,8-tri(p-tosyl)-1,4,8,11-tetraazacyclotetradecan-1-yl]-methyl}-1,1',1''-triphenylmethane in the step g of Example 1, with the exception of 3,3'-(phenyl)methylenedibenzyl bromide in the step g of Example 1 being substituted with 4,4'-(4-methyl-phenyl)methylenedibenzyl bromide obtained in the step a above, MS[M]+=1608.2 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.85-1.96 (br m, 8H), 2.12 (s, 3H), 3.09-3.44 (br m, 32H), 4.13 (s, 4H), 5.53 (s, 1H), 6.98-7.24 (m, 12H); FAB-MS (m/z): 683.2 [M+H]$^+$.

Example 9

Preparation of 4,4'-bis[(1,4,8,11-tetraazacyclotetradecan-1-yl)-methyl]-4"-bromo-1,1',1"-triphenylmethane octahydrobromide dihydrate

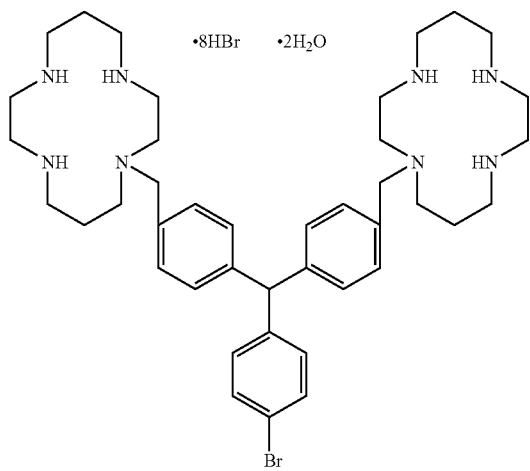 [SMILES: Brc1ccc(C(c2ccc(CN3CCCNCCNCCCNCC3)cc2)c2ccc(CN3CCCNCCNCCCNCC3)cc2)cc1 ; "·8HBr" ; "·2H2O"]

a. 4,4'-(4-Bromo-phenyl)methylenedibenzyl bromide 0.56 g of a colorless oily substance was obtained by the method for preparing 3,3'-(phenyl)methyldibenzyl bromide in Example 1, with the exception of o-bromobenzaldehyde in the step a of Example 1 being substituted with p-bromobenzaldehyde and then methyl benzoate in the step b of Example 1 being substituted with methyl p-bromobenzoate, MS[M]+=509.1 m/e.

b. 4,4'-Bis{[1,4,8-tri(p-tosyl)-1,4,8,11-tetraazacyclotetradecan-1-yl]methyl}-4"-bromo-1,1',1"-triphenylmethane A white foamy solid was obtained by the method of preparing 3,3'-bis{[1,4,8-tri(p-tosyl)-1,4,8,11-tetraazacyclotetradecan-1-yl]-methyl}-1,1',1"-triphenylmethane in the step g of Example 1, with the exception of 3,3'-(phenyl)methylenedibenzyl bromide in the step g of Example 1 being substituted with 4,4'-(4-bromo-phenyl)methylenedibenzyl bromide obtained in the step a above, MS[M]+=1673.1 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.98-2.08 (br m, 8H), 3.05-3.41 (br m, 32H), 4.03 (s, 4H), 5.80 (s, 1H), 7.13-7.49 (m, 12H); FAB-MS (m/z): 747.2 [M+H]$^+$.

Example 10

Preparation of 4,4'-bis[(1,4,8,11-tetraazacyclotetradecan-1-yl)-methyl]-4"-fluoro-1,1',1"-triphenylmethane octahydrobromide dihydrate

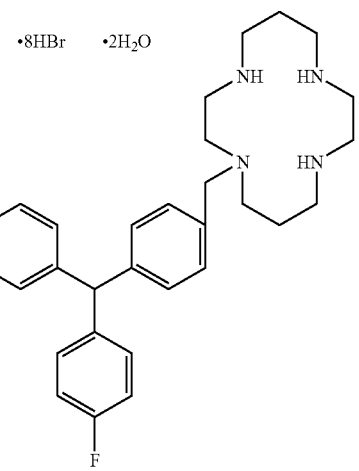

a. 4,4'-(4-Fluoro-phenyl)methylenedibenzyl bromide 0.56 g of a colorless oily substance was obtained by the method for preparing 3,3'-(phenyl)methyldibenzyl bromide in Example 1, with the exception of o-bromobenzaldehyde in the step a of Example 1 being substituted with p-bromobenzaldehyde and then methyl benzoate in the step b of Example 1 being substituted with methyl p-fluorobenzoate, MS[M]+=448.2 m/e.

b. 4,4'-Bis {[1,4,8-tri(p-tosyl)-1,4,8,11-tetraazacyclotetradecan-1-yl]-methyl}-4"-fluoro-1,1',1"-triphenylmethane A white foamy solid was obtained by the method of preparing 3,3'-bis{[1,4,8-tri(p-tosyl)-1,4,8,11-tetraazacyclotetradecan-1-yl]-methyl }-1,1',1"-triphenylmethane in the step g of Example 1, with the exception of 3,3'-(phenyl)methylenedibenzyl bromide in the step g of Example 1 being substituted with 4,4'-(4-fluoro-phenyl)methylenedibenzyl bromide obtained in the step a above, MS[M]+=1612.2 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.73-1.99 (br m, 8H), 3.09-3.50 (br m, 32H), 4.11 (s, 4H), 5.60 (s, 1H), 6.94-7.28 (m, 12H); FAB-MS (m/z): 687.2 [M+H]$^+$.

Example 11

Preparation of 4,4'-bis[(1,4,8,11-tetraazacyclotetradecan-1-yl)-methyl]-3"-chloro-1,1',1"-triphenylmethane octahydrobromide dihydrate

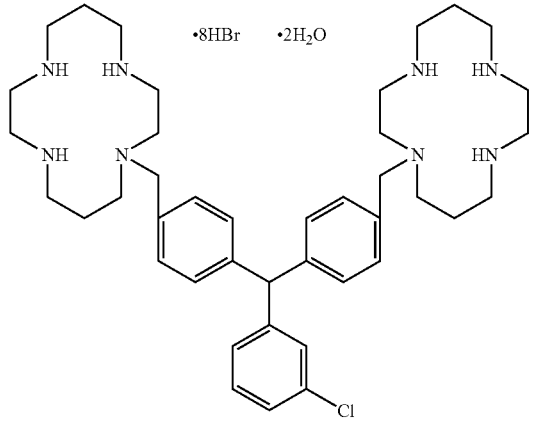 [SMILES: Clc1cccc(C(c2ccc(CN3CCCNCCNCCCNCC3)cc2)c2ccc(CN3CCCNCCNCCCNCC3)cc2)c1 ; "·8HBr" ; "·2H2O"]

a. 4,4'-(3-Chloro-phenyl)methylenedibenzyl bromide 0.56 g of a colorless oily substance was obtained by the method of preparing 3,3'-(phenyl)methyldibenzyl bromide in Example 1, with the exception of o-bromobenzaldehyde in the step a of Example 1 being substituted with p-bromobenzaldehyde and then methyl benzoate in the step b of Example 1 being substituted with methyl m-chlorobenzoate, MS[M]+=464.6 m/e.

b. 4,4'-Bis{[1,4,8-tri(p-tosyl)-1,4,8,11-tetraazacyclotetradecan-1-yl]methyl}-3"-chloro-1,1',1"-triphenylmethane A white foamy solid was obtained by the method for preparing 3,3'-bis{[1,4,8-tri(p-tosyl)-1,4,8,11-tetraazacyclotetradecan-1-yl]-methyl }-1,1',1"-triphenylmethane in the step g of Example 1, with the exception of 3,3'-(phenyl)methylenedibenzyl bromide in the step g of Example 1 being substituted with 4,4'-(3-chloro-phenyl)methylenedibenzyl bromide obtained in the step a above, MS[M]+=1628.7 m/e.

c. Deprotection with a Mixed Acid

The title compound in straw yellow solid was obtained by the method in the step k of Example 1, with the exception of the starting material in the step k of Example 1 being substituted with the intermediate obtained in the step b above.

$^1$H-NMR (400 MHz, D$_2$O) δppm: 1.84-1.98 (br m, 8H), 3.08-3.29 (br m, 32H), 4.11 (s, 4H), 5.58 (s, 1H), 6.99-7.25 (m, 12H); FAB-MS (m/z): 703.2 [M+H]$^+$.

Example 12

Preparation of 3,3'-bis[(1,4,7,10-tetraazacyclododecan-1-yl)-methyl]-1,1',1"-triphenylmethane octahydrochloride

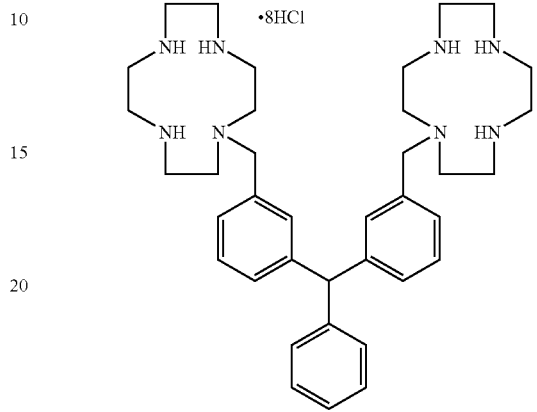

a. 1,4,7,10-tetraazacyclododecane

A white solid product was obtained by the method of preparing 1,4,8,11-tetraazacyclotetradecane in Example 1, with the exception of di(3-aminopropyl)-ethyldiamine being substituted with triethyltetraamine, MS[M]+=172.3 m/e.

b. 1,4,7-tri(trifluoroacetyl)-1,4,7,10-tetraazacyclododecane 1,4,7,10-Tetraazacyclododecane (10 mmol) was dissolved in methanol (15 ml). To the system was added triethylamine (2 ml), and then slowly dropwise added at room temperature ethyl trifluoroacetate (50 mmol). Upon the completion of dropwise addition, the mixture was allowed to react at room temperature over night, concentrated and then column separated (eluant: ethyl acetate) to obtain 4.1 g of a white solid, yield 89%, MS[M]+=460.3 m/e.

c. 3,3'-Bis{[1,4,7-tri(trifluoroacetyl)-1,4,7,10-tetraazacyclododecan-1-yl]-methyl}-1,1',1"-triphenylmethane The intermediate (2 mmol) obtained from the step b above, the intermediate 3,3'-(phenyl)methylenedibenzyl bromide (1 mmol) obtained from the step e of Example 1, anhydrous potassium carbonate (3 mmol) and dried acetonitrile (20 ml) were heat refluxed with intensive stir for 24 hours, stood, filtrated. The filtrate was concentrated and column separated (eluant: dichloromethane/methanol system) to obtain 0.8 g of a white foamy solid, yield 67%, MS[M]+=1189.0 m/e.

k. Deprotection with Anhydrous K$_2$CO$_3$

The intermediate (0.3 mmol) obtained from the step c above was dissolved in dried methanol (3 ml). To the system was added anhydrous K$_2$CO$_3$ (2 mmol). The mixture was refluxed over night. To the mixture was added toluene (20 ml). The reaction liquor was azeotropic refluxed to remove methanol, stood until room temperature, filtrated by suction, concentrated, dried in vacuum over night, dissolved with a small amount of methanol and ethyl ether. To the resultant was introduced into HCl gas for 0.5 h. A solid was precipitate, filtrated by suction, washed with ethyl ether to obtain 0.15 g of the title compound as straw yellow solid, yield 55%.

$^1$H-NMR (400 MHz, D$_2$O) δppm: 2.63-2.91 (br m, 32H), 3.60 (s, 4H), 5.58 (s, 1H), 6.95-7.21 (m, 13H); FAB-MS (m/z): 613.2 [M+H]$^+$.

Example 13

Preparation of 3,3'-bis{[3,7,11-triaza-dicyclo[11.3.1] heptadecan-1(16),13(17),14-trien-7-yl]-methyl}-1,1', 1''-triphenylmethane hexahydrobromide dihydrate

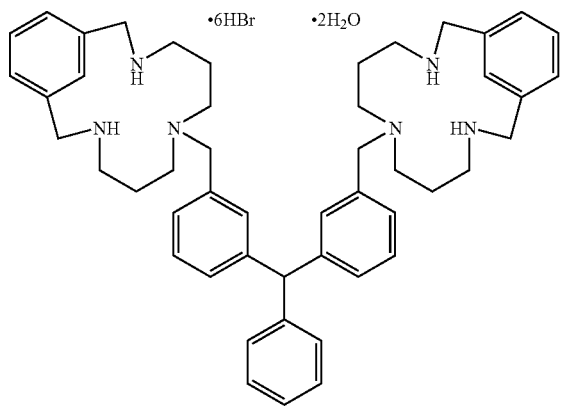

a. N-diethoxyphosphoryl-3,3'-iminodipropyl cyanide 3,3'-Iminodipropyl cyanide (50 mmol) was dissolved in dichloromethane (100 ml). To the system was added triethylamine (10 ml), and then dropwise added at room temperature diethoxyphosphoryl chloride (50 mmol) in dicholormethane (60 ml) solution. The mixture was allowed to react at room temperature over night. The resultant was concentrated and performed to column chromatography (eluant: dichloromethane/methanol system) to obtain 9.7 g of a colorless transparent oily substance, yield 75%, MS[M]+=259.2 m/e.

b. N-diethoxyphosphoryl-N,N'-di(p-tosyl)3,3'-iminodipropylamine

The intermediate (20 mmol) obtained in the step a above was dissolved in methanolic ammonia solution (200 ml). To the system was added Raney nickel alloy (20 g) as catalyst. The reactant was catalytically hydrogenated at room temperature and 45 Psi for 48 hours. The reaction was terminated. The resultant was filtrated, concentrated, dried in vacuum, and dissolved in dichloromethane (200 ml). To the resultant solution was added triethylamine (6 ml), dropwise added p-tosyl chloride (40 mmol) in dichloromethane (100 ml) solution. The mixture was allowed to react at room temperature over night, filtrated, concentrated, column separated (eluant: dichloromethane/methanol system) to obtain 6.0 g of a white solid, yield 52%; MS[M]+=577.7 m/e.

c. [3,11-di(p-tosyl)-3,7,11-triaza-dicyclo[11.3.1] heptadecan-1(16),13(17),14-trien-7-yl]-diethoxy-phosphate The intermediate (20 mmol) obtained in the step b above was dissolved in acetonitrile (500 ml). To the solution was added anhydrous K$_2$CO$_3$. The mixture was refluxed for 1 hour. To the system was slowly added the compound of formula 1,3-dibromotoluene (20 mmol) in acetonitrile (120 ml) solution. The mixture was refluxed for 24 hours, stood until room temperature, filtrated, concentrated and column separated (eluant: dichloromethane/methanol system) to obtain 8.5 g of a white solid compound of formula 16 [3,11-di(p-tosyl)-3,7,11-triaza-dicyclo[11.3.1]heptadecan-1(16), 13(17),14-trien-7-yl]-diethoxyphosphate, yield 63%. MS[M]+=677.8 m/e.

d. 3,11-Di(p-tosyl)-3,7,11-triaza-dicyclo[11.3.1] heptadecan-1(16),13(17),14-triene The intermediate (2 mmol) obtained in the step c above was dissolved in glacial acetic acid (10 mmol). To the solution was added 45% glacial acetic acid solution of HBr (3 ml) (commercially available from Alfa). The mixture was stirred at room temperature for 2 hours. To the mixture was added a large amount of ethyl ether (200 ml). A solid was precipitated, filtrated by suction to give an orange solid. The solid was dissolved with dichloromethane (150 ml). The organic phase was washed with 10 mol/L NaOH solution (50 ml) and saturated sodium chloride aqueous solution, respectively, dried (Na$_2$SO$_4$), filtrated, concentrated and column separated (eluant: dichloromethane/methanol system) to obtain 0.76 g of a white solid compound; yield 70%, MS[M]+=541.7 m/e.

e. 3,3'-Bis{[3,11-di(tosyl)3,7,11-triaza-dicyclo [11.3.1]heptadecan-1(16),13(17),14-trien-7-yl]-methyl}-1,1',1''-triphenylmethane The intermediate (2 mmol) obtained in the step d above, the intermediate 3,3'-(phenyl)methylenedibenzyl bromide (1 mmol) obtained in the step e of Example 1, anhydrous potassium carbonate (3 mmol) and dried acetonitrile (20 ml) were heat refluxed with intensive stir for 24 hours, stood, filtrated. The filtrate was concentrated and column separated (eluant: dichloromethane/methanol system) to obtain 1.1 g of a white foamy solid, yield 84%, MS[M]+=1351.8 m/e.

f. Deprotection with a Mixed Acid

The intermediate (0.3 mmol) obtained in the step e was refluxed for 48 hours in a mixed liquor of hydrobromic acid and glacial acetic acid (volume ratio: 2/3, 10 ml). The reactant was stood until room temperature. To the resultant was added a great deal of acetone. A white solid was precipitated, filtrated, washed with acetone to obtain 0.31 g of title compound, straw yellow solid, yield 81%.

$^1$H-NMR (400 MHz, D$_2$O) δppm: 1.44 (br, 4H), 1.88-1.90 (br m, 4H), 2.72-2.84 (br m, 16H), 4.00 (s, 4H), 4.20 (s, 8H), 5.55 (s, 1H), 7.14-8.52 (m, 21H); FAB-MS (m/z): 735.1 [M+H]$^+$.

Example 14

Preparation of 3,3'-bis{[3,7,11-triaza-dicyclo[11.3.1]heptadecan-1(16),13(17),14-trien-7-yl]-methyl}-4"-methyl-1,1',1"-triphenylmethane hexahydrobromide dihydrate

Example 15

Preparation of 3,3'-bis{[3,7,11-triaza-dicyclo[11.3.1]heptadecan-1(16),13(17),14-trien-7-yl]-methyl}-4"-bromo-1,1',1"-triphenylmethane hexahydrobromide dihydrate

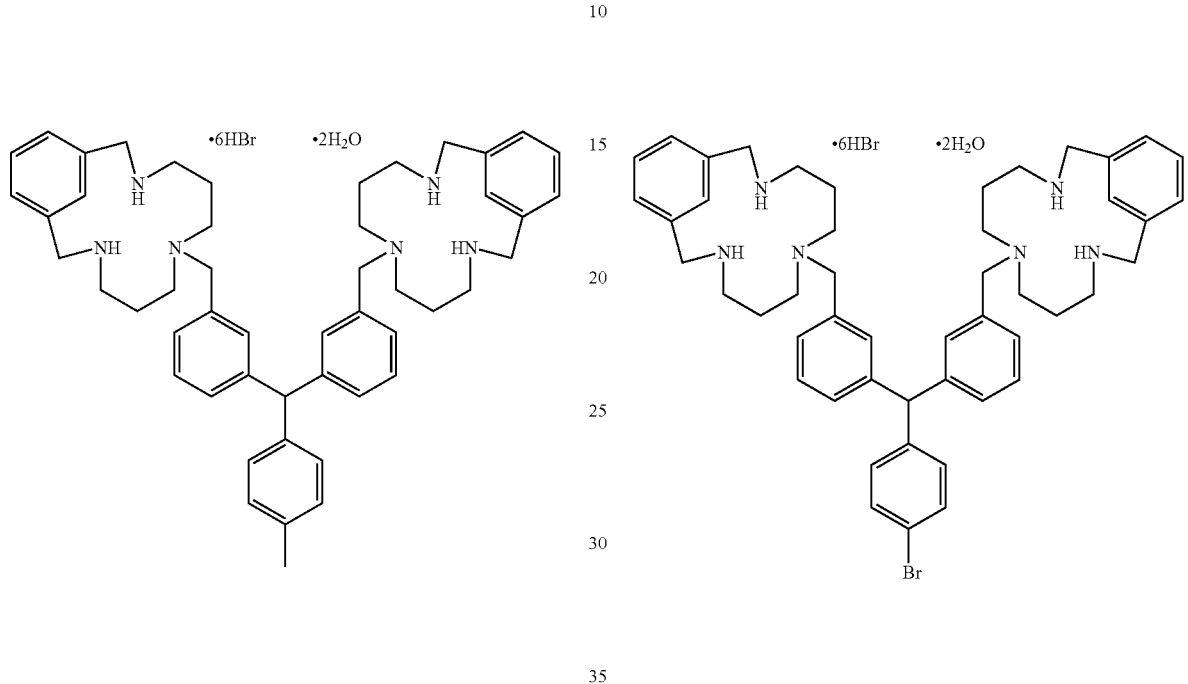

a. 3,3'-Bis {[3,11-di(p-tosyl)-3,7,11-triaza-dicyclo[11.3.1]heptadecan-1(16),13(17),14-trien-7-yl]-methyl}-4"-methyl-1,1',1"-triphenylmethane A white foamy solid was obtained by the method in the step e of Example 13, with the exception of 3,3'(phenyl)methylenedibenzyl bromide in the step e of Example 13 being substituted with the intermediate 3,3'-(4-methyl-phenyl)methylenedibenzyl bromide in the step a of Example 2, MS[M]+=1365.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.47 (br, 4H), 2.12 (s, 3H), 1.93-2.09 (br m, 4H), 2.76-3.01 (br m, 16H), 4.03 (s, 4H), 4.23 (s, 8H), 5.53 (s, 1H), 7.03-7.58 (m, 20H); FAB-MS (m/z): 749.1 [M+H]$^+$.

a. 3,3'-Bis {[3,11-di(p-tosyl)-3,7,11-triaza-dicyclo[11.3.1]heptadecan-1(16),13(17),14-trien-7-yl]-methyl}-4"-bromo-1,1',1"-triphenylmethane A white foamy solid was obtained by the method in the step e of Example 13, with the exception of 3,3'(phenyl)methylenedibenzyl bromide in the step e of Example 13 being substituted with the intermediate 3,3'-(4-bromo-phenyl)methylenedibenzyl bromide in the step a of Example 3, MS[M]+=1430.7 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.47 (br, 4H), 1.90-2.00 (br m, 4H), 2.75-2.89 (br m, 16H), 4.03 (s, 4H), 4.23 (s, 8H), 5.56 (s, 1H), 7.09-7.47 (m, 20H); FAB-MS (m/z): 814.0 [M+H]$^+$.

Example 16

Preparation of 3,3'-bis{[3,7,11-triaza-dicyclo[11.3.1] heptadecan-1(16),13(17),14-trien-7-yl]-methyl}-4''-fluoro-1,1',1''-triphenylmethane hexahydrobromide dihydrate

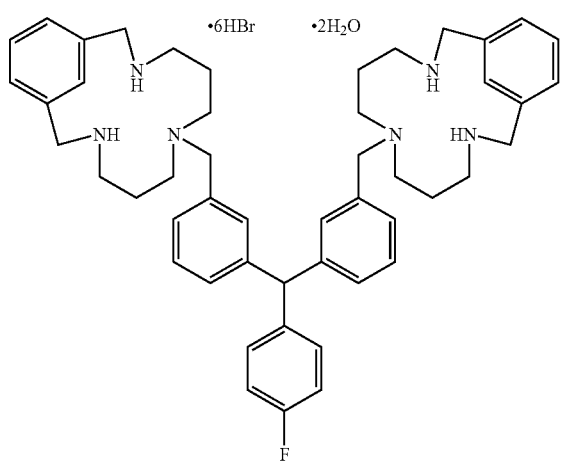 [SMILES: Fc1ccc(C(c2cccc(CN3CCCNCc4cccc(c4)CNCCC3)c2)c2cccc(CN3CCCNCc4cccc(c4)CNCCC3)c2)cc1 ; "·6HBr" ; "·2H2O"]

a. 3,3'-Bis {[3,11-di(p-tosyl)-3,7,11-triaza-dicyclo[11.3.1]heptadecan-1(16),13(17),14-trien-7-yl]-methyl}-4''-fluoro-1,1',1''-triphenylmethane A white foamy solid was obtained by the method in the step e of Example 13, with the exception of 3,3'-(phenyl)methylenedibenzyl bromide in the step e of Example 13 being substituted with the intermediate 3,3'-(4-fluoro-phenyl)methylenedibenzyl bromide in the step a of Example 4, MS[M]+=1369.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.48-1.54 (br m, 4H), 1.93-2.01 (br m, 4H), 2.74-2.86 (br m, 16H), 4.00 (s, 4H), 4.23 (s, 8H), 5.55 (s, 1H), 7.02-7.58 (m, 20H); FAB-MS (m/z): 753.1 [M+H]$^+$.

Example 17

Preparation of 3,3'-bis{[3,7,11-triaza-dicyclo[11.3.1] heptadecan-1(16),13(17),14-trien-7-yl]-methyl}-3''-chloro-1,1',1''-triphenylmethane hexahydrobromide dihydrate

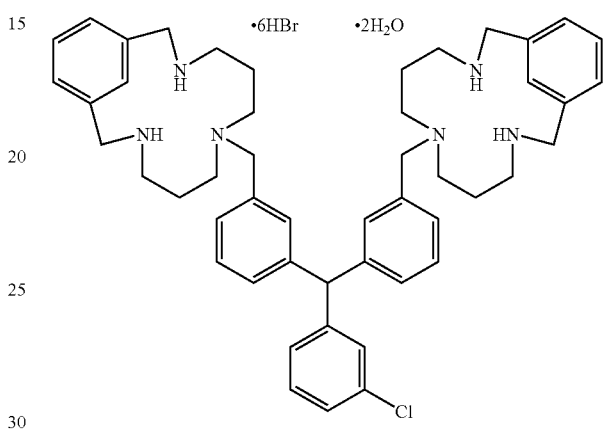

a. 3,3'-Bis {[3,11-di(p-tosyl)-3,7,11-triaza-dicyclo[11.3.1]heptadecan-1(16), 13(17),14-trien-7-yl]-methyl}-3''-chloro-1,1',1''-triphenylmethane A white foamy solid was obtained by the method in the step e of Example 13, with the exception of 3,3'(phenyl)methylenedibenzyl bromide in the step e of Example 13 being substituted with the intermediate 3,3'-(3-chloro-phenyl)methylenedibenzyl bromide in the step a of Example 5, MS[M]+=1386.3 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.49 (br, 4H), 1.95 (br, 4H), 2.75-2.88 (br m, 16H), 4.03 (s, 4H), 4.24 (s, 8H), 5.59 (s, 1H), 7.11-7.84 (m, 20H); FAB-MS (m/z): 769.5 [M+H]$^+$.

Example 18

Preparation of 2-{[3,3'-bis((3,7,11-triaza-dicyclo[11.3.1]heptadecan-1(16),13(17),14-trien-7-yl)-methyl)-1,1'yl]-diphenyl}methylenepyridyl hexahydrobromide dihydrate

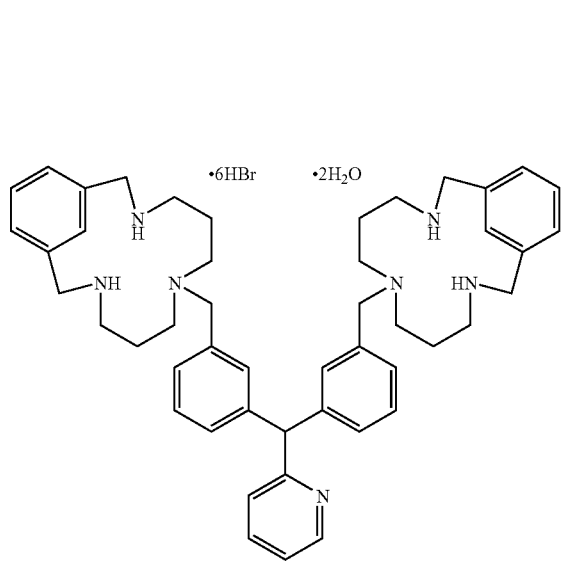 [SMILES: c1ccc(C(c2cccc(CN3CCCNCc4cccc(c4)CNCCC3)c2)c2cccc(CN3CCCNCc4cccc(c4)CNCCC3)c2)nc1 ; "·6HBr" ; "·2H2O"]

a. 2-{[3,3'-Bis((3,11-di(p-tosyl)-3,7,11-triaza-dicyclo[11.3.1]heptadecan-1(16),13(17),14-trien-7-yl]-methyl)-1,1'yl)-diphenyl}methylene pyridine A white foamy solid was obtained by the method in the step e of Example 13, with the exception of 3,3'(phenyl)methylenedibenzyl bromide in the step e of Example 13 being substituted with the intermediate 3,3'-(pyridyl-2-yl)methylenedibenzyl bromide in the step a of Example 6, MS[M]+=1352.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.57 (br, 4H), 2.02 (br, 4H), 2.85-3.15 (br m, 16H), 4.10 (s, 4H), 4.28 (s, 8H), 5.68 (s, 1H), 7.10-7.64 (m, 20H); FAB-MS (m/z): 736.1 [M+H]$^+$.

Example 19

Preparation of 3,3'-bis{[3,7,11,17-tetraaza-dicyclo[11.3.1]heptadecan-1(16),13(17),14-trien-7-yl]-methyl}-1,1',1"-triphenyl methane hexahydrobromide dihydrate

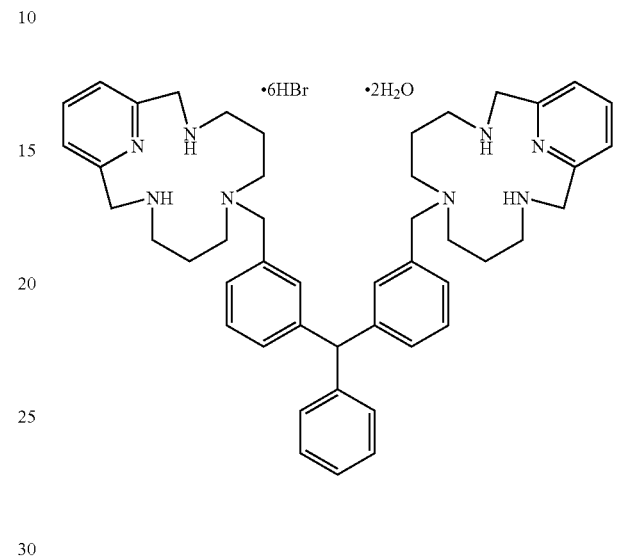

a. 3,11-di(p-tosyl)-3,7,11,17-tetraaza-dicyclo[11.3.1]heptadecan-1(16),13(17),14-triene A white solid was obtained by the method for preparing the intermediate 3,11-di(p-tosyl)-3,7,11-triaza-dicyclo[11.3.1]heptadecan-1(16),13(17),14-triene in Example 13, with the exception of 1,3-dibromomethyl benzene in the step c of Example 13 being substituted with 2,6-dibromomethyl pyridine, MS[M]+=542.7 m/e.

b. 3,3'-Bis{[3,11-di(tosyl)-3,7,11,17-tetraaza-dicyclo[11.3.1]heptadecan-1(16),13(17),14-trien-7-yl]-methyl}-1,1',1"-triphenylmethane The intermediate (2 mmol) obtained in the step a above, the intermediate 3,3'-(phenyl)methylenedibenzyl bromide (1 mmol) obtained from the step e of Example 1, anhydrous potassium carbonate (3 mmol) and dried acetonitrile (20 ml) were heat refluxed with intensive stir for 24 hours, stood, filtrated. The filtrate was concentrated and column separated (eluant: dichloromethane/methanol system) to obtain 0.8 g of a white foamy solid, yield 59%, MS[M]+=1353.8 m/e.

c. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 2.11-2.15 (br m, 8H), 2.98-3.16 (br m, 16H), 4.22 (s, 4H), 4.40 (s, 8H), 5.64 (s, 1H), 7.17-7.87 (m, 19H); FAB-MS (m/z): 737.1 [M+H]$^+$.

Example 20

Preparation of 3,3'-bis{[3,7,11,17-tetraaza-dicyclo[11.3.1]heptadecan-1(16),13(17),14-trien-7-yl]-methyl}-4"-methyl-1,1',1"-triphenylmethane hexahydrobromide dihydrate

Example 21

Preparation of 3,3'-bis{[3,7,11,17-tetraaza-dicyclo[11.3.1]heptadecan-1(16),13(17),14-trien-7-yl]-methyl}-4"-bromo-1,1',1"-triphenylmethane hexahydrobromide dihydrate

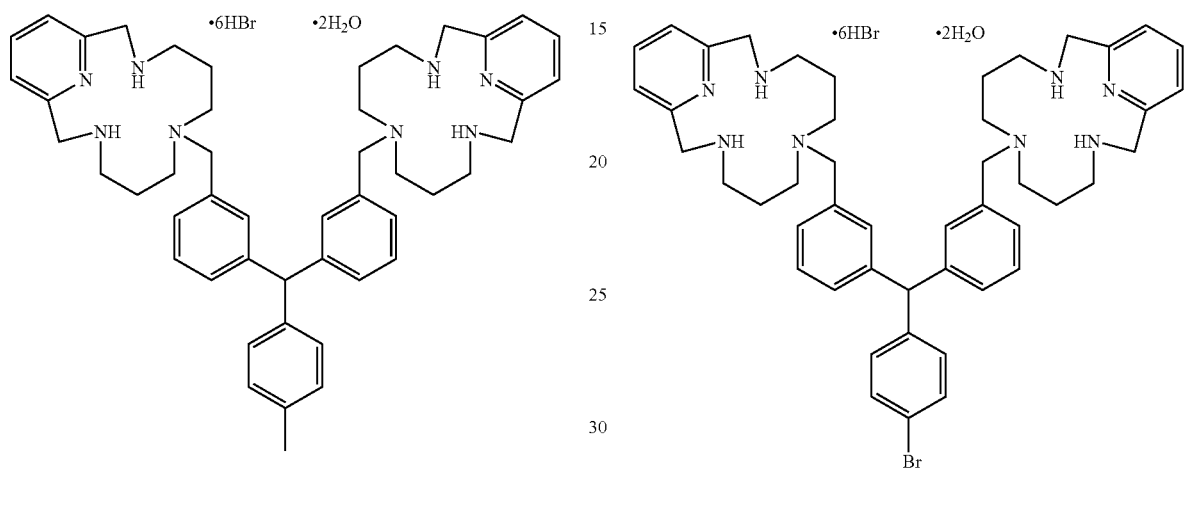

a. 3,3'-Bis{[3,11-di(p-tosyl)-3,7,11,17-tetraaza-dicyclo[11.3.1]heptadecan-1(16),13(17),14-trien-7-yl]-methyl}-4"-methyl-1,1',1"-triphenylmethane A white foamy solid was obtained by the method for preparing 3,3'-bis{[3,11-di(p-tosyl)-3,7,11,17-tetraaza-dicyclo[11.3.1]heptadecan-1(16),13(17),14-trien-7-yl]-methyl}-1,1',1"-triphenylmethane in the step b of Example 19, with the exception of 3,3'-(phenyl)methylenedibenzyl bromide being substituted with the intermediate 3,3'-(4-methyl-phenyl)methylenedibenzyl bromide obtained in the step a of Example 2, MS[M]+=1367.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.
$^1$H-NMR (400 MHz, D$_2$O) δppm: 2.19-2.21 (br m, 8H), 2.26 (s, 3H) 3.07-3.28 (br m, 16H), 4.27 (s, 4H), 4.48 (s, 8H), 5.66 (s, 1H), 7.07-7.98 (m, 18H); FAB-MS (m/z): 751.1 [M+H]$^+$.

a. 3,3'-Bis {[3,11-di(p-tosyl)-3,7,11,17-tetraaza-dicyclo[11.3.1]heptadecan-1(16),13(17),14-trien-7-yl]-methyl}-4"-bromo-1,1',1"-triphenylmethane A white foamy solid was obtained by the method for preparing 3,3'-bis{[3,11-di(p-tosyl)-3,7,11,17-tetraaza-dicyclo[11.3.1]heptadecan-1(16),13(17),14-trien-7-yl]-methyl}-1,1',1"-triphenylmethane in the step b of Example 19, with the exception of 3,3'-(phenyl)methylenedibenzyl bromide being substituted with the intermediate 3,3'-(4-bromo-phenyl)methylenedibenzyl bromide obtained in the step a of Example 3, MS[M]+=1432.7 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.
$^1$H-NMR (400 MHz, D$_2$O) δppm: 2.01-2.06 (br m, 8H), 2.92-3.13 (br m, 16H), 4.11 (s, 4H), 4.33 (s, 8H), 5.53 (s, 1H), 7.07-7.82 (m, 18H); FAB-MS (m/z): 816.0 [M+H]$^+$.

Example 22

Preparation of 3,3'-bis{[3,7,11,17-tetraaza-dicyclo[11.3.1]heptadecan-1(16),13(17),14-trien-7-yl]-methyl}-4"-fluoro-1,1',1"-triphenylmethane hexahydrobromide dihydrate

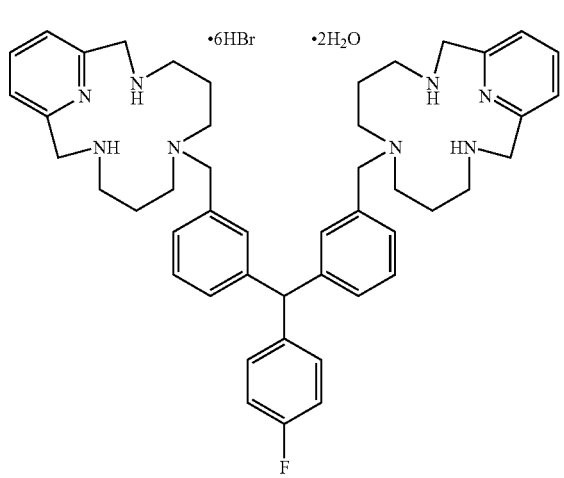 [SMILES: Fc1ccc(C(c2cccc(CN3CCCNCc4cccc(n4)CNCCC3)c2)c2cccc(CN3CCCNCc4cccc(n4)CNCCC3)c2)cc1 ; "·6HBr" ; "·2H2O"]

a. 3,3'-Bis {[3,11-di(p-tosyl)-3,7,11,17-tetraaza-dicyclo[11.3.1]heptadecan-1(16),13(17),14-trien-7-yl]-methyl}-4"-fluoro-1,1',1"-triphenylmethane A white foamy solid was obtained by the method for preparing 3,3'-bis{[3,11-di(p-tosyl)-3,7,11,17-tetraaza-dicyclo[11.3.1]heptadecan-1(16),13(17),14-trien-7-yl]-methyl}-1,1',1"-triphenylmethane in the step b of Example 19, with the exception of 3,3'-(phenyl)methylenedibenzyl bromide being substituted with the intermediate 3,3'-(4-fluoro-phenyl)methylenedibenzyl bromide obtained in the step a of Example 4, MS[M]+=1371.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 2.03-2.07 (br m, 8H), 2.91-2.95 (br m, 16H), 4.08 (s, 4H), 4.32 (s, 8H), 5.53 (s, 1H), 6.90-7.82 (m, 18H); FAB-MS (m/z): 755.1 [M+H]$^+$.

Example 23

Preparation of 3,3'-bis{[3,7,11,17-tetraaza-dicyclo[11.3.1]heptadecan-1(16),13(17),14-trien-7-yl]-methyl}-3"-chloro-1,1',1"-triphenylmethane hexahydrobromide dihydrate

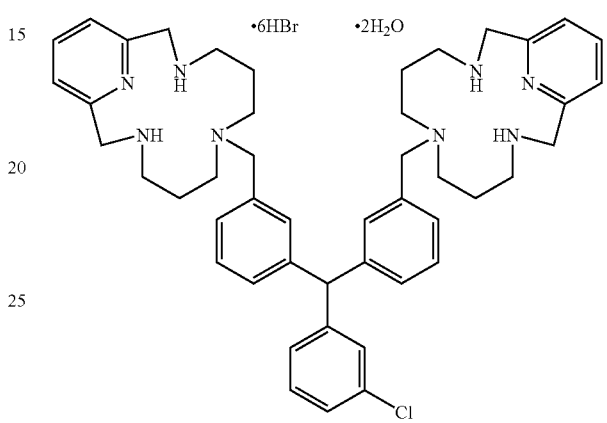

a. 3,3'-Bis {[3,11-di(p-tosyl)-3,7,11,17-tetraaza-dicyclo[11.3.1]heptadecan-1(16),13(17),14-trien-7-yl]-methyl}-3"-chloro-1,1',1"-triphenylmethane A white foamy solid was obtained by the method of preparing 3,3'-bis{[3,11-di(p-tosyl)-3,7,11,17-tetraaza-dicyclo[11.3.1]heptadecan-1(16),13(17),14-trien-7-yl]-methyl}-1,1',1"-triphenylmethane in the step b of Example 19, with the exception of 3,3'-(phenyl)methylenedibenzyl bromide being substituted with the intermediate 3,3'-(3-chloro-phenyl)methylenedibenzyl bromide obtained in the step a of Example 5, MS[M]+=1388.3 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 2.08-2.14 (br m, 8H), 3.01-3.18 (br m, 16H), 4.12 (s, 4H), 4.36 (s, 8H), 5.57 (s, 1H), 7.12-7.87 (m, 18H); FAB-MS (m/z): 771.5 [M+H]$^+$.

Example 24

Preparation of 2-{[3,3'-bis((3,7,11,17-tetraaza-dicyclo[11.3.1]heptadecan-1(16),13(17),14-trien-7-yl)-methyl)-1,1'yl]-diphenyl}methylenepyridyl hexahydrobromide dihydrate

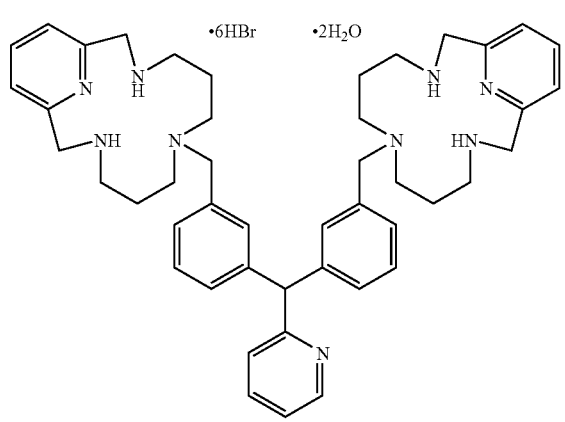

a. 2-{[3,3'-bis([3,11-di(p-tosyl)-3,7,11,17-tetraazadicyclo[11.3.1]heptadecan-1(16),13(17),14-trien-7-yl]-methyl)-1,1'yl]-diphenyl}methylenepyridine A white foamy solid was obtained by the method for preparing 3,3'-bis{[3,11-di(p-tosyl)-3,7,11,17-tetraazadicyclo[11.3.1]heptadecan-1(16),13(17),14-trien-7-yl]-methyl}-1,1',1"-triphenylmethane in the step b of Example 19, with the exception of 3,3'-(phenyl)methylenedibenzyl bromide being substituted with the intermediate 3,3'-(pyrid-2-yl)methylenedibenzyl bromide obtained in the step a of Example 6, MS[M]+=1354.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 2.01-2.13 (br m, 8H), 2.96-3.13 (br m, 16H), 4.18 (s, 4H), 4.35 (s, 8H), 6.02 (s, 1H), 7.20-8.48 (m, 18H); FAB-MS (m/z): 738.0 [M+H]$^+$.

Example 25

Preparation of 4,4'-bis{[3,7,11-triaza-dicyclo[11.3.1]heptadecan-1(16),13(17),14-trien-7-yl]-methyl}-1,1'1"-triphenylmethane hexahydrobromide dihydrate

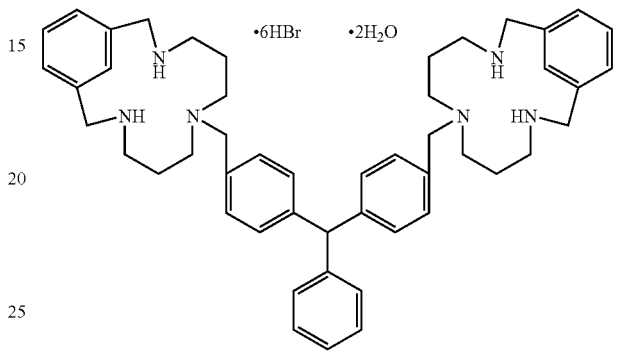

a. 4,4'-Bis{[3,11-di(p-tosyl)-3,7,11-triaza-dicyclo[11.3.1]heptadecan-1(16),13(17),14-trien-7-yl]-methyl}-1,1'1"-triphenylmethane A white foamy solid was obtained by the method for preparing 3,3'-bis{[3,11-di(p-tosyl)-3,7,11-triaza-dicyclo[11.3.1]heptadecan-1(16),13(17),14-trien-7-yl]-methyl}-1,1',1"-triphenylmethane in the step e of Example 13, with the exception of 3,3'-(phenyl)methylenedibenzyl bromide being substituted with the intermediate 4,4'-(phenyl)methylenedibenzyl bromide obtained in the step a of Example 7, MS[M]+=1351.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.57 (br, 4H), 1.96-2.00 (br m, 4H), 2.80-2.92 (br m, 16H), 4.04 (s, 4H), 4.24 (s, 8H), 5.53 (s, 1H), 7.07-7.46 (m, 21H); FAB-MS (m/z): 735.1 [M+H]$^+$.

Example 26

Preparation of 4,4'-bis{[3,7,11-triaza-dicyclo[11.3.1]heptadecan-1(16),13(17),14-trien-7-yl]-methyl}-4"-methyl-1,1'1"-triphenylmethane hexahydrobromide dihydrate

Example 27

Preparation of 4,4'-bis{[3,7,11-triaza-dicyclo[11.3.1]heptadecan-1(16),13(17),14-trien-7-yl]-methyl}-4"-bromo-1,1'1"-triphenylmethane hexahydrobromide dihydrate

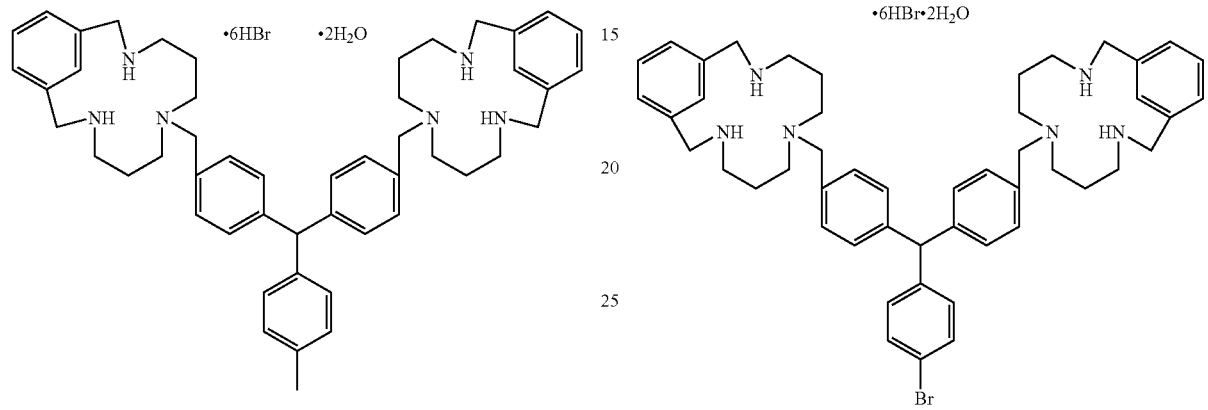

a. 4,4'-Bis{[3,11-di(p-tosyl)-3,7,11-triaza-dicyclo[11.3.1]heptadecan-1(16),13(17),14-trien-7-yl]-methyl}-4"-methyl-1,1'1"-triphenylmethane A white foamy solid was obtained by the method for preparing 3,3'-bis{[3,11-di(p-tosyl)-3,7,11-triaza-dicyclo[11.3.1]heptadecan-1(16),13(17),14-trien-7-yl]-methyl}-1,1',1"-triphenylmethane in the step e of Example 13, with the exception of 3,3'-(phenyl)methylenedibenzyl bromide being substituted with the intermediate 4,4'-(4-methyl-phenyl)methylenedibenzyl bromide obtained in the step a of Example 8, MS[M]+=1365.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.52 (br, 4H), 2.01-2.07 (br m, 4H), 2.10 (s, 3H), 2.80-2.92 (br m, 16H), 4.01 (s, 4H), 4.24 (s, 8H), 5.48 (s, 1H), 6.92-7.60 (m, 20H); FAB-MS (m/z): 749.1 [M+H]$^+$.

a. 4,4'-Bis{[3,11-di(p-tosyl)-3,7,11-triaza-dicyclo[11.3.1]heptadecan-1(16),13(17),14-trien-7-yl]-methyl}-4"-bromo-1,1'1"-triphenylmethane A white foamy solid was obtained by the method for preparing 3,3'-bis{[3,11-di(p-tosyl)-3,7,11-triaza-dicyclo[11.3.1]heptadecan-1(16),13(17),14-trien-7-yl]-methyl}-1,1',1"-triphenylmethane in the step e of Example 13, with the exception of 3,3'-(phenyl)methylenedibenzyl bromide being substituted with the intermediate 4,4'-(4-bromo-phenyl)methylenedibenzyl bromide obtained in the step a of Example 9, MS[M]+=1430.7 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.52-1.63 (br m, 4H), 1.95-2.01 (br m, 4H), 2.79-2.91 (br m, 16H), 4.02 (s, 4H), 4.23 (s, 8H), 5.51 (s, 1H), 7.04-7.58 (m, 20H); FAB-MS (m/z): 814.0 [M+H]$^+$.

Example 28

Preparation of 4,4'-bis{[3,7,11-triaza-dicyclo[11.3.1] heptadecan-1(16),13(17),14-trien-7-yl]-methyl}-4"-fluoro-1,1'1"-triphenylmethane hexahydrobromide dihydrate

Example 29

Preparation of 4,4'-bis{[3,7,11-triaza-dicyclo[11.3.1] heptadecan-1(16),13(17),14-trien-7-yl]-methyl}-3"-chloro-1,1'1"-triphenylmethane hexahydrobromide dihydrate

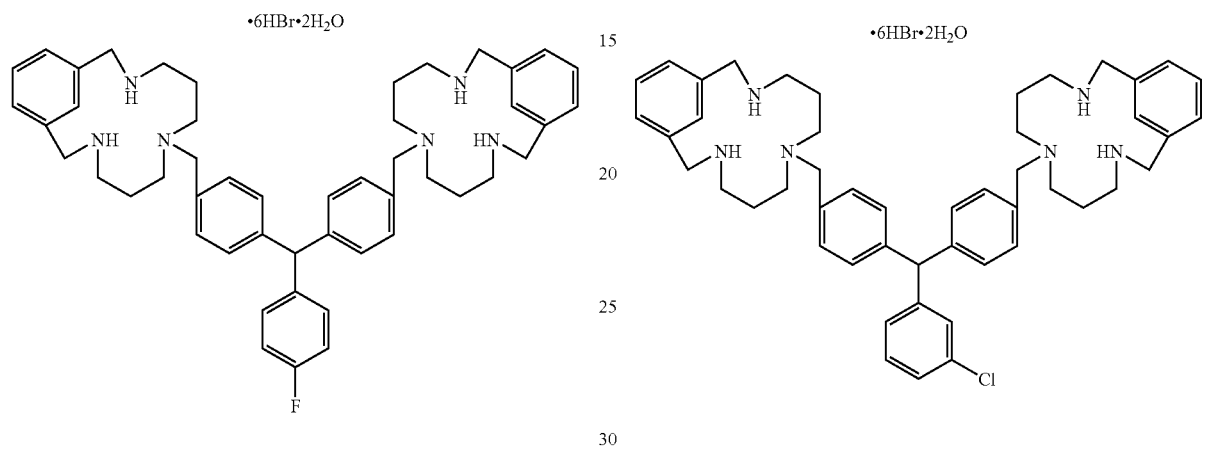

a. 4,4'-Bis{[3,11-di(p-tosyl)-3,7,11-triaza-dicyclo[11.3.1]heptadecan-1(16),13(17),14-trien-7-yl]-methyl}-4"-fluoro-1,1'1"-triphenylmethane A white foamy solid was obtained by the method for preparing 3,3'-bis{[3,11-di(p-tosyl)-3,7,11-triaza-dicyclo[11.3.1]heptadecan-1(16),13(17),14-trien-7-yl]-methyl}-1,1',1"-triphenylmethane in the step e of Example 13, with the exception of 3,3'-(phenyl)methylenedibenzyl bromide being substituted with the intermediate 4,4'-(4-fluoro-phenyl)methylenedibenzyl bromide obtained in the step a of Example 10, MS[M]+=1369.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.70 (br, 4H), 2.15-2.18 (br m, 4H), 2.97-3.27 (br m, 16H), 4.19 (s, 4H), 4.41 (s, 8H), 5.78 (s, 1H), 7.32-7.65 (m, 20H); FAB-MS (m/z): 753.1 [M+H]$^+$.

a. 4,4'-Bis{[3,11-di(p-tosyl)-3,7,11-triaza-dicyclo[11.3.1]heptadecan-1(16),13(17),14-trien-7-yl]-methyl}-3"-chloro-1,1'1"-triphenylmethane A white foamy solid was obtained by the method for preparing 3,3'-bis{[3,11-di(p-tosyl)-3,7,11-triaza-dicyclo[11.3.1]heptadecan-1(16),13(17),14-trien-7-yl]-methyl}-1,1',1"-triphenylmethane in the step e of Example 13, with the exception of 3,3'-(phenyl)methylenedibenzyl bromide being substituted with the intermediate 4,4'-(3-chloro-phenyl)methylenedibenzyl bromide obtained in the step a of Example 11, MS[M]+=1386.3 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.52 (br, 4H), 1.89-2.00 (br m, 4H), 2.82-3.10 (br m, 16H), 4.05 (s, 4H), 4.24 (s, 8H), 5.53 (s, 1H), 7.06-7.46 (m, 20H); FAB-MS (m/z): 769.5 [M+H]$^+$.

Example 30

Preparation of 4,4'-bis{[3,7,11,17-tetraaza-dicyclo[11.3.1]heptadecan-1(16),13(17),14-trien-7-yl]-methyl}-1,1',1''-triphenyl methane hexahydrobromide dihydrate

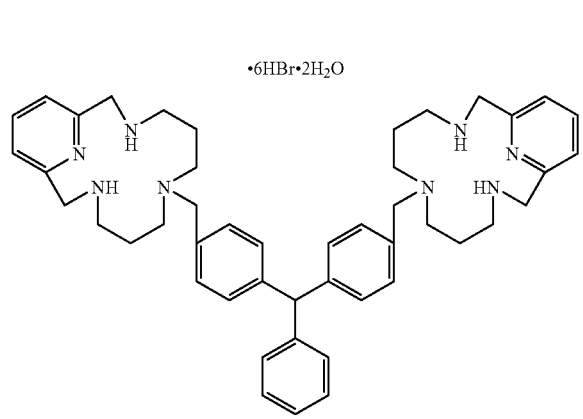 [SMILES: c1ccc(C(c2ccc(CN3CCCNCc4cccc(n4)CNCCC3)cc2)c2ccc(CN3CCCNCc4cccc(n4)CNCCC3)cc2)cc1 ; "·6HBr·2H2O"]

a. 4,4'-Bis {[3,11-di(p-tosyl)-3,7,11,17-tetraaza-dicyclo[11.3.1]heptadecan-1(16),13(17),14-trien-7-yl]-methyl}-1,1',1''-triphenylmethane A white foamy solid was obtained by the method for preparing 3,3'-bis{[3,11-di(p-tosyl)-3,7,11,17-tetraaza-dicyclo[11.3.1]heptadecan-1(16),13(17),14-trien-7-yl]-methyl}-1,1',1''-triphenylmethane in the step b of Example 19, with the exception of 3,3'-(phenyl)methylenedibenzyl bromide being substituted with the intermediate 4,4'-(phenyl)methylenedibenzyl bromide obtained in the step a of Example 7, MS[M]+=1353.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 2.28 (br m, 8H), 3.14-3.30 (br m, 16H), 4.30 (s, 4H), 4.51 (s, 8H), 5.72 (s, 1H), 7.28-7.98 (m, 19H); FAB-MS (m/z): 737.1 [M+H]$^+$.

Example 31

Preparation of 4,4'-bis{[3,7,11,17-tetraaza-dicyclo[11.3.1]heptadecan-1(16),13(17),14-trien-7-yl]-methyl}-4''-methyl-1,1',1''-triphenylmethane hexahydrobromide dihydrate

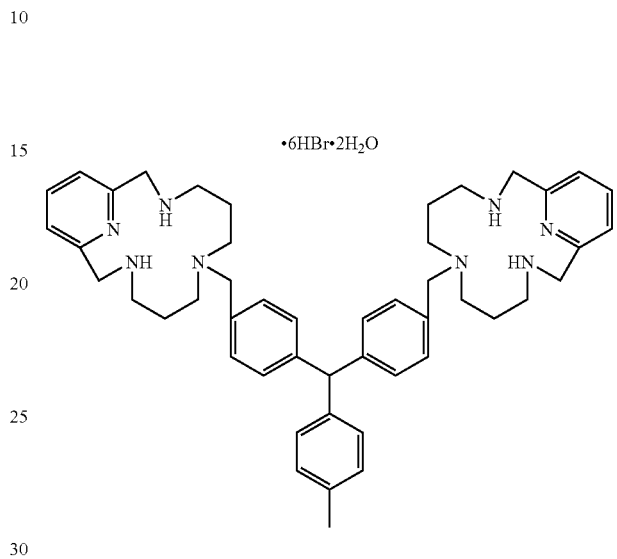

a. 4,4'-Bis {[3,11-di(p-tosyl)-3,7,11,17-tetraaza-dicyclo[11.3.1]heptadecan-1(16),13(17),14-trien-7-yl]-methyl}-4''-methyl-1,1',1''-triphenylmethane A white foamy solid was obtained by the method for preparing 3,3'-bis{[3,11-di(p-tosyl)-3,7,11,17-tetraaza-dicyclo[11.3.1]heptadecan-1(16),13(17),14-trien-7-yl]-methyl}-1,1',1''-triphenylmethane in the step b of Example 19, with the exception of 3,3'-(phenyl)methylenedibenzyl bromide being substituted with the intermediate 4,4'-(4-methyl-phenyl)methylenedibenzyl bromide obtained in the step a of Example 8, MS[M]+=1367.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 1.98 (s, 3H), 2.06 (br, 8H), 2.92-3.09 (br m, 16H), 4.05 (s, 4H), 4.28 (s, 8H), 5.48 (s, 1H), 7.03-7.78 (m, 18H); FAB-MS (m/z): 751.1 [M+H]$^+$.

Example 32

Preparation of 4,4'-bis{[3,7,11,17-tetraaza-dicyclo[11.3.1]heptadecan-1(16),13(17),14-trien-7-yl]-methyl}-4"-bromo-1,1',1"-triphenylmethane hexahydrobromide dihydrate

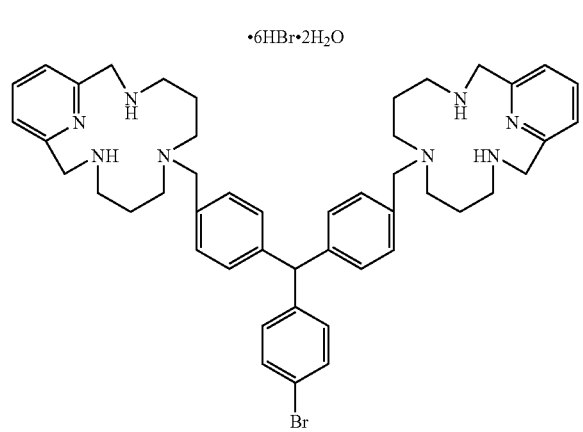 [SMILES: Brc1ccc(C(c2ccc(CN3CCCNCc4cccc(n4)CNCCC3)cc2)c2ccc(CN3CCCNCc4cccc(n4)CNCCC3)cc2)cc1 ; "·6HBr·2H2O"]

a. 4,4'-Bis {[3,11-di(p-tosyl)-3,7,11,17-tetraaza-dicyclo[11.3.1]heptadecan-1(16),13(17),14-trien-7-yl]-methyl}-4"-bromo-1,1',1"-triphenylmethane A white foamy solid was obtained by the method for preparing 3,3'-bis{[3,11-di(p-tosyl)-3,7,11,17-tetraaza-dicyclo[11.3.1]heptadecan-1(16),13(17),14-trien-7-yl]-methyl}-1,1',1"-triphenylmethane in the step b of Example 19, with the exception of 3,3'-(phenyl)methylenedibenzyl bromide being substituted with the intermediate 4,4'-(4-bromo-phenyl)methylenedibenzyl bromide obtained in the step a of Example 9, MS[M]+=1432.7 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 2.09 (br m, 8H), 2.93-3.09 (br m, 16H), 4.10 (s, 4H), 4.30 (s, 8H), 5.47 (s, 1H), 6.93-7.78 (m, 18H); FAB-MS (m/z): 816.0 [M+H]$^+$.

Example 33

Preparation of 4,4'-bis{[3,7,11,17-tetraaza-dicyclo[11.3.1]heptadecan-1(16),13(17),14-trien-7-yl]-methyl}-4"-fluoro-1,1',1"-triphenylmethane hexahydrobromide dihydrate

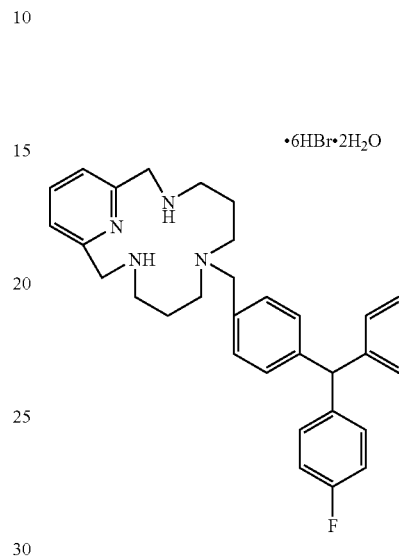

a. 4,4'-Bis {[3,11-di(p-tosyl)-3,7,11,17-tetraaza-dicyclo[11.3.1]heptadecan-1(16),13(17),14-trien-7-yl]-methyl}-4"-fluoro-1,1',1"-triphenylmethane A white foamy solid was obtained by the method for preparing 3,3'-bis{[3,11-di(p-tosyl)-3,7,11,17-tetraaza-dicyclo[11.3.1]heptadecan-1(16),13(17),14-trien-7-yl]-methyl}-1,1',1"-triphenylmethane in the step b of Example 19, with the exception of 3,3'-(phenyl)methylenedibenzyl bromide being substituted with the intermediate 4,4'-(4-fluoro-phenyl)methylenedibenzyl bromide obtained in the step a of Example 10, MS[M]+=1371.8 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.

$^1$H-NMR (400 MHz, D$_2$O) δppm: 2.15 (br m, 8H), 3.01-3.16 (br m, 16H), 4.17 (s, 4H), 4.37 (s, 8H), 5.70 (s, 1H), 7.12-7.84 (m, 18H); FAB-MS (m/z): 755.1 [M+H]$^+$.

Example 34

Preparation of 4,4'-bis{[3,7,11,17-tetraaza-dicyclo[11.3.1]heptadecan-1(16),13(17),14-trien-7-yl]-methyl}-3''-chloro-1,1',1''-triphenylmethane hexahydrobromide dihydrate

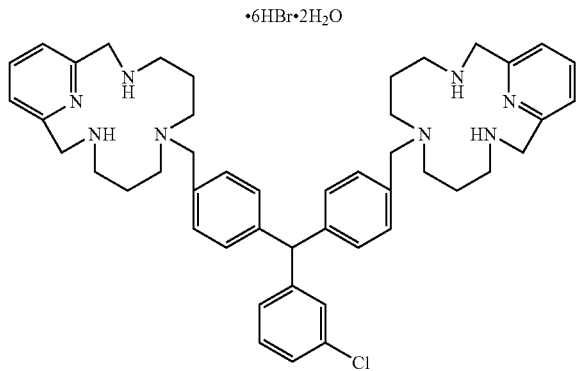 [SMILES: Clc1cccc(C(c2ccc(CN3CCCNCc4cccc(n4)CNCCC3)cc2)c2ccc(CN3CCCNCc4cccc(n4)CNCCC3)cc2)c1 ; "·6HBr·2H2O"]

a. 4,4'-Bis {[3,11-di(p-tosyl)-3,7,11,17-tetraaza-dicyclo[11.3.1]heptadecan-1(16),13(17),14-trien-7-yl]-methyl}-3''-chloro-1,1',1''-triphenylmethane A white foamy solid was obtained by the method of preparing 3,3'-bis{[3,11-di(p-tosyl)-3,7,11,17-tetraaza-dicyclo[11.3.1]heptadecan-1(16),13(17),14-trien-7-yl]-methyl}-1,1',1''-triphenylmethane in the step b of Example 19, with the exception of 3,3'-(phenyl)methylenedibenzyl bromide being substituted with the intermediate 4,4'-(3-chloro-phenyl)methylenedibenzyl bromide obtained in the step a of Example 11, MS[M]+=1388.3 m/e.

b. Deprotection with a Mixed Acid

The title compound in straw yellow solid was obtained by the method in the step k of Example 1, with the exception of the starting material in the step k of Example 1 being substituted with the intermediate obtained in the step a above.
$^1$H-NMR (400 MHz, D$_2$O) δppm: 2.07 (br m, 8H), 2.92-3.08 (br m, 16H), 4.08 (s, 4H), 4.29 (s, 8H), 5.52 (s, 1H), 7.02-7.78 (m, 19H); FAB-MS (m/z): 771.5 [M+H]$^+$.

The HIV-1 inhibition activity of the compounds according to the invention can be detected by following methods:

Example 35

The Evaluation of Anti-HIV Activity of the Compounds of the Invention

Per well of polystyrene plate (Immulon IB, Dynex Technology, Chantilly, Va.) was applied with HIV IG (a buffer of 0.085 M sodium carbonate and sodium bicarbonate, pH=9.6), stood at 4° C. over night, washed with PBS-T buffer (0.01 M PBS contains 0.05% Tween-20). The reaction was terminated with PBS containing 1% skimmed milk (Bio-Rad Inc., Hercules, Calif.). A virus dissolved product was added to the wells, incubated at 37° C. for 1 hour, and washed. To the washed wells were added anti-P24 mAb (183-12H-5C), biotin labeled antimouse IgG1 (Santa Cruz Biotech., Santa Cruz, Calif.), SA-HRP and TMB successively. The reaction was terminated with 1N H$_2$SO$_4$. The absorption was detected at 450 nm by means of ELISA detector (Ultra 384, Tecan). Recombination protein p24 (US Biological, Swampscott, Mass.) was considered when the response curve of standard dosage was established. The inhibition activity IC$_{50}$ (half inhibition concentration) values of p24 protein and (cell pathological effect) CPE were calculated by Calcusyn software provided by Sloan-Kettering Cancer Center (New York).

Example 36

To 100 μl solution per compound on 96 wells cultivation plate at a certain concentration was added the same volume of cells (5×10$^5$/ml). Incubation was performed at 37° C. for 4 days. To the resultant were added 50 μl XTT solution (1 mg/ml) and 0.02 nM PMS. After the incubation was performed for 4 hours, the absorption was detected at 450 nm by means of ELISA detector. The CC$_{50}$ (half toxic concentration) value was calculated by Calcusyn software provided by Sloan-Kettering Cancer Center (New York).

The inhibition activity (IC$_{50}$) of pathological effect (CPE) and cytotoxicity (CC$_{50}$) of p24 antigens and cells of HIV-1 of the compounds of part of examples were shown as follows:

| Example No. | IC$_{50}$ (μM) p24 | IC$_{50}$ (μM) CPE | CC$_{50}$ (μM) |
|---|---|---|---|
| 1 | 0.13 ± 0.02 | 0.41 ± 0.11 | 321.50 ± 7.13 |
| 2 | 0.17 ± 0.08 | 0.48 ± 0.31 | 285.49 ± 18.84 |
| 3 | 0.13 ± 0.01 | 0.08 ± 0.04 | 160.90 ± 4.23 |
| 4 | 0.32 ± 0.02 | 0.42 ± 0.06 | 366.63 ± 54.04 |
| 5 | 0.35 ± 0.04 | 0.23 ± 0.01 | 162.04 ± 2.69 |
| 6 | 0.16 ± 0.04 | 0.55 ± 0.16 | 377.46 ± 34.35 |
| 7 | 0.98 ± 0.12 | 2.42 ± 0.40 | 101.02 ± 1.05 |
| 8 | 0.97 ± 0.14 | 2.05 ± 0.58 | 130.02 ± 12.40 |
| 9 | 0.43 ± 0.07 | 1.75 ± 0.37 | 65.77 ± 7.96 |
| 10 | 0.43 ± 0.11 | 1.22 ± 0.20 | 91.28 ± 8.75 |
| 11 | 0.65 ± 0.20 | 1.48 ± 0.52 | 67.75 ± 13.29 |
| 13 | 0.64 ± 0.08 | 1.56 ± 0.48 | 12.44 ± 3.69 |
| 19 | 0.44 ± 0.04 | 0.79 ± 0.02 | 14.54 ± 1.29 |
| 23 | 0.32 ± 0.05 | 1.18 ± 0.48 | 15.28 ± 0.56 |
| 25 | 0.55 ± 0.09 | 1.87 ± 0.28 | 32.53 ± 3.27 |
| 31 | 0.78 ± 0.18 | 1.07 ± 0.79 | 39.29 ± 0.08 |
| 32 | 0.15 ± 0.02 | 0.80 ± 0.23 | 12.88 ± 0.31 |

The invention claimed is:
1. A compound of formula (I),

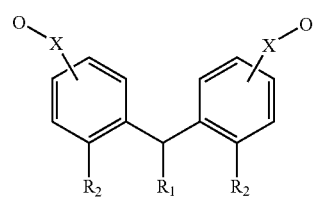

wherein:
O represents a macro ring which is
(1,4,8,11-tetraazacyclotetradecan-1-yl);
(1,4,7,10-tetraazacyclododecan-1-yl);
[3,7,11-triaza-dicyclo[11.3.1]heptadecan-1(16),13(17),14-trien-7-yl]; or
[3,7,11,17-tetraaza-dicyclo[11.3.1]heptadecan-1(16),13(17),14-trien-7-yl];

R₁ represents a radical selected from the group consisting of: hydrogen, halogen; perfluoroalkyl; alkoxyalkyl; amino; alkylamino; dialkylamino; amido; alkylaminoalkyl; unsubstituted or substituted, saturated or unsaturated straight or branched alkyl; carboxyl; substituted or unsubstituted phenyl, the substituents of the phenyl being at least one radical selected from the group consisting of: hydroxyl, alkoxy, alkoxyalkyl, halogen, perfluoroalkyl, thio, nitro, carboxyalkyl, alkoxycarbonyl, alkoxycarbonylalkyl, carboxyamido, carboxyamidoalkyl, alkyl, cycloalkyl, alkylthio, alkylsulfinyl, alkylsulfonyl, aminosulfonyl, amidino, cyano, amino, amido, alkylamino, dialkylamino, alkylaminoalkyl, or alkoxy mono-substituted by substituent selected from the group consisting of carboxyl, amino, alkylamino or dialkylamino; cycloalkyl; or heterocyclic radical selected from the group consisting of: pyridyl, thienyl, pyrazolyl, tetrazolyl, furyl, pyrrolyl, imidazolyl, triazolyl and thiazolyl;

R₂ represents a radical selected from the group consisting of: hydrogen, hydroxyl, mercapto, alkoxy, carboxyl, carboxyalkyl, amino, alkylamino, dialkylamino, carboxyamido, carboxyamidoalkyl, aminosulfonyl or acetamido; and X represents a divalent linking radical selected from the group consisting of: —N=CH—, —CH=N—, —(CH₂)ₙ—NH—, —NH—(CH₂)—, —(CH₂)ₙ—, —CH=CH— or —N=N—, n is an integer from 1 to 8, or an optical isomer, a pharmaceutically acceptable salt, or a hydrate thereof.

2. The compound according to claim 1 having formulae II or III:

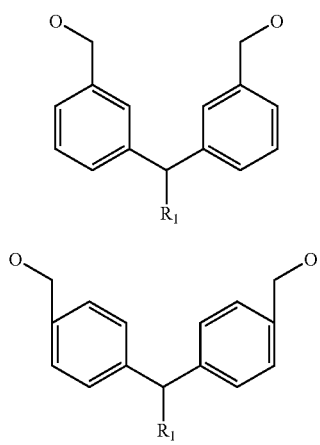

wherein:
O represents a macro ring which is
(1,4,8,11-tetraazacyclotetradecan-1-yl);
(1,4,7,10-tetraazacyclododecan-1-yl);
[3,7,11-triaza-dicyclo[11.3.1]heptadecan-1(16),13(17), 14-trien-7-yl]; or
[3,7,11,17-tetraaza-dicyclo[11.3.1]heptadecan-1(16),13 (17),14-trien-7-yl]; and R₁ represents a radical selected from the group consisting of: hydrogen, halogen; perfluoroalkyl; alkoxyalkyl; amino; alkylamino; dialkylamino; amido; alkylaminoalkyl; unsubstituted or substituted, saturated or unsaturated straight or branched alkyl; carboxyl; substituted or unsubstituted phenyl, the substituents of the phenyl being at least one radical selected from the group consisting of: hydroxyl, alkoxy, alkoxyalkyl, halogen, perfluoroalkyl, thio, nitro, carboxyalkyl, alkoxycarbonyl, alkoxycarbonylalkyl, carboxyamido, carboxyamidoalkyl, alkyl, cycloalkyl, alkylthio, alkylsulfinyl, alkylsulfonyl, aminosulfonyl, amidino, cyano, amino, amido, alkylamino, dialkylamino, alkylaminoalkyl, or alkoxy mono-substituted by substituent selected from the group consisting of carboxyl, amino, alkylamino or dialkylamino; cycloalkyl; or heterocyclic radical selected from the group consisting of: pyridyl, thienyl, pyrazolyl, tetrazolyl, furyl, pyrrolyl, imidazolyl, triazolyl and thiazolyl.

3. The compound according to claim 1 which is selected from the group consisting of:
3,3'-bis[(1,4,8,11-tetraazacyclotetradecan-1-yl)-methyl]-1,1',1"-triphenylmethane;
3,3'-bis[(1,4,8,11-tetraazacyclotetradecan-1-yl)-methyl]-4"-methyl-1,1',1"-triphenylmethane;
3,3'-bis[(1,4,8,11-tetraazacyclotetradecan-1-yl)-methyl]-4"-bromo-1,1',1"-triphenylmethane;
3,3'-bis[(1,4,8,11-tetraazacyclotetradecan-1-yl)-methyl]-4"-fluoro-1,1',1"-triphenylmethane;
3,3'-bis[(1,4,8,11-tetraazacyclotetradecan-1-yl)-methyl]-3"-chloro-1,1',1"-triphenylmethane;
2-{[3,3'-bis[(1,4,8,11-tetraazacyclotetradecan-1-yl)-methyl]-1,1'yl]-diphenyl}-methylene pyridine;
4,4'-bis[(1,4,8,11-tetraazacyclotetradecan-1-yl)-methyl]-1,1',1"-triphenylmethane;
4,4'-bis[(1,4,8,11-tetraazacyclotetradecan-1-yl)-methyl]-4"-methyl-1,1',1"-triphenylmethane;
4,4'-bis[(1,4,8,11-tetraazacyclotetradecan-1-yl)-methyl]-4"-bromo-1,1',1"-triphenylmethane;
4,4'-bis[(1,4,8,11-tetraazacyclotetradecan-1-yl)-methyl]-4"-fluoro-1,1',1"-triphenylmethane;
4,4'-bis[(1,4,8,11-tetraazacyclotetradecan-1-yl)-methyl]-3"-chloro-1,1',1"-triphenylmethane;
3,3'-bis[(1,4,7,10-tetraazacyclododecan-1-yl)-methyl]-1,1',1"-triphenylmethane octahydrochloride;
3,3'-bis{[3,7,11-triaza-dicyclo[11.3.1]heptadecan-1(16),13(17),14-trien-7-yl]-methyl}-1,1',1"-triphenylmethane;
3,3'-bis{[3,7,11-triaza-dicyclo[11.3.1]heptadecan-1(16),13(17),14-trien-7-yl]-methyl}-4"-methyl-1,1',1"-triphenylmethane;
3,3'-bis{[3,7,11-triaza-dicyclo[11.3.1]heptadecan-1(16),13(17),14-trien-7-yl]-methyl}-4"-bromo-1,1',1"-triphenylmethane;
3,3'-bis{[3,7,11-triaza-dicyclo[11.3.1]heptadecan-1(16),13(17),14-trien-7-yl]-methyl}-4"-fluoro-1,1',1"-triphenylmethane;
3,3'-bis{[3,7,11-triaza-dicyclo[11.3.1]heptadecan-1(16),13(17),14-trien-7-yl]-methyl}-3"-chloro-1,1',1"-triphenylmethane;
2-{[3,3'-bis((3,7,11-triaza-dicyclo[11.3.1]heptadecan-1(16),13(17),14-trien-7-yl)-methyl)-1,1'yl]-diphenyl}methylene pyridine;
3,3'-bis{[3,7,11,17-tetraaza-dicyclo[11.3.1]heptadecan-1(16),13(17),14-trien-7-yl]-methyl}-1,1',1"-triphenylmethane;
3,3'-bis{[3,7,11,17-tetraaza-dicyclo[11.3.1]heptadecan-1(16),13(17),14-trien-7-yl]-methyl}-4"-methyl-1,1',1"-triphenylmethane;
3,3'-bis{[3,7,11,17-tetraaza-dicyclo[11.3.1]heptadecan-1(16),13(17),14-trien-7-yl]-methyl}-4"-bromo-1,1',1"-triphenylmethane;

3,3'-bis{[3,7,11,17-tetraaza-dicyclo[11.3.1]heptadecan-1 (16),13(17),14-trien-7-yl]-methyl}-4"-fluoro-1,1',1"-triphenylmethane;
3,3'-bis{[3,7,11,17-tetraaza-dicyclo[11.3.1]heptadecan-1 (16),13(17),14-trien-7-yl]-methyl}-3"-chloro-1,1',1"-triphenylmethane;
2-{[3,3'-bis((3,7,11,17-tetraaza-dicyclo[11.3.1]heptadecan-1(16),13(17),14-trien-7-yl)-methyl)-1,1'yl]-diphenyl}methylene pyridine;
4,4'-bis{[3,7,11-triaza-dicyclo[11.3.1]heptadecan-1(16), 13(17),14-trien-7-yl]-methyl}-1,1',1"-triphenylmethane;
4,4'-bis{[3,7,11-triaza-dicyclo[11.3.1]heptadecan-1(16), 13(17),14-trien-7-yl]-methyl}-4"-methyl-1,1',1"-triphenylmethane;
4,4'-bis{[3,7,11-triaza-dicyclo[11.3.1]heptadecan-1(16), 13(17),14-trien-7-yl]-methyl}-4"-bromo-1,1',1"-triphenylmethane;
4,4'-bis{[3,7,11-triaza-dicyclo[11.3.1]heptadecan-1(16), 13(17),14-trien-7-yl]-methyl}-4"-fluoro-1,1',1"-triphenylmethane;
4,4'-bis{[3,7,11-triaza-dicyclo[11.3.1]heptadecan-1(16), 13(17),14-trien-7-yl]-methyl}-3"-chloro-1,1',1"-triphenylmethane;
4,4'-bis{[3,7,11,17-tetraaza-dicyclo[11.3.1]heptadecan-1 (16),13(17),14-trien-7-yl]-methyl}-1,1',1"-triphenylmethane;
4,4'-bis{[3,7,11,17-tetraaza-dicyclo[11.3.1]heptadecan-1 (16),13(17),14-trien-7-yl]-methyl}-4"-methyl-1,1',1"-triphenylmethane;
4,4'-bis{[3,7,11,17-tetraaza-dicyclo[11.3.1]heptadecan-1 (16),13(17),14-trien-7-yl]-methyl}-4"-bromo-1,1',1"-triphenylmethane;
4,4'-bis{[3,7,11,17-tetraaza-dicyclo[11.3.1]heptadecan-1 (16),13(17),14-trien-7-yl]-methyl}-4"-fluoro-1,1',1"-triphenylmethane; and
4,4'-bis{[3,7,11,17-tetraaza-dicyclo[11.3.1]heptadecan-1 (16),13(17),14-trien-7-yl]-methyl}-3"-chloro-1,1',1"-triphenylmethane.

4. The compound according to claim 1 wherein the pharmaceutically acceptable salt or hydrate of the compound is selected from the group consisting of:
3,3'-bis[(1,4,8,11-tetraazacyclotetradecan-1-yl)-methyl]-1,1',1"-triphenylmethane octahydrobromide dihydrate;
3,3'-bis[(1,4,8,11-tetraazacyclotetradecan-1-yl)-methyl]-4"-methyl-1,1',1"-triphenylmethane octahydrobromide dihydrate;
3,3'-bis[(1,4,8,11-tetraazacyclotetradecan-1-yl)-methyl]-4"-bromo-1,1',1"-triphenylmethane octahydrobromide dihydrate;
3,3'-bis[(1,4,8,11-tetraazacyclotetradecan-1-yl)-methyl]-4"-fluoro-1,1',1"-triphenylmethane octahydrobromide dihydrate;
3,3'-bis[(1,4,8,11-tetraazacyclotetradecan-1-yl)-methyl]-3"-chloro-1,1',1"-triphenylmethane octahydrobromide dihydrate;
2-{[3,3'-bis[(1,4,8,11-tetraazacyclotetradecan-1-yl)-methyl]-1,1'yl]-diphenyl}methylene pyridine octahydrobromide dihydrate;
4,4'-bis[(1,4,8,11-tetraazacyclotetradecan-1-yl)-methyl]-1,1',1"-triphenylmethane octahydrobromide dihydrate;
4,4'-bis[(1,4,8,11-tetraazacyclotetradecan-1-yl)-methyl]-4"-methyl-1,1',1"-triphenylmethane octahydrobromide dihydrate;
4,4'-bis[(1,4,8,11-tetraazacyclotetradecan-1-yl)-methyl]-4"-bromo-1,1',1"-triphenylmethane octahydrobromide dihydrate;
4,4'-bis[(1,4,8,11-tetraazacyclotetradecan-1-yl)-methyl]-4"-fluoro-1,1',1"-triphenylmethane octahydrobromide dihydrate;
4,4'-bis[(1,4,8,11-tetraazacyclotetradecan-1-yl)-methyl]-3"-chloro-1,1',1"-triphenylmethane octahydrobromide dihydrate;
3,3'-bis[(1,4,7,10-tetraazacyclododecan-1-yl)-methyl]-1, 1',1"-triphenylmethane octahydrochloride;
3,3'-bis{[3,7,11-triaza-dicyclo[11.3.1]heptadecan-1(16), 13(17),14-trien-7-yl]-methyl}-1,1',1"-triphenylmethane hexahydrobromide dihydrate;
3,3'-bis{[3,7,11-triaza-dicyclo[11.3.1]heptadecan-1(16), 13(17),14-trien-7-yl]-methyl}-4"-methyl-1,1',1"-triphenylmethane hexahydrobromide dihydrate;
3,3'-bis{[3,7,11-triaza-dicyclo[11.3.1]heptadecan-1(16), 13(17),14-trien-7-yl]-methyl}-4"-bromo-1,1',1"-triphenylmethane hexahydrobromide dihydrate;
3,3'-bis{[3,7,11-triaza-dicyclo[11.3.1]heptadecan-1(16), 13(17),14-trien-7-yl]-methyl}-4"-fluoro-1,1',1"-triphenylmethane hexahydrobromide dihydrate;
3,3'-bis{[3,7,11-triaza-dicyclo[11.3.1]heptadecan-1(16), 13(17),14-trien-7-yl]-methyl}-3"-chloro-1,1',1"-triphenylmethane hexahydrobromide dihydrate;
2-{[3,3'-bis((3,7,11-triaza-dicyclo[11.3.1]heptadecan-1 (16),13(17),14-trien-7-yl)-methyl)-1,1'yl]-diphenyl}methylene pyridine hexahydrobromide dihydrate;
3,3'-bis{[3,7,11,17-tetraaza-dicyclo[11.3.1]heptadecan-1 (16),13(17),14-trien-7-yl]-methyl}-1,1',1"-triphenylmethane hexahydrobromide dihydrate;
3,3'-bis{[3,7,11,17-tetraaza-dicyclo[11.3.1]heptadecan-1 (16),13(17),14-trien-7-yl]-methyl}-4"-methyl-1,1',1"-triphenylmethane hexahydrobromide dihydrate;
3,3'-bis{[3,7,11,17-tetraaza-dicyclo[11.3.1]heptadecan-1 (16),13(17),14-trien-7-yl]-methyl}-4"-bromo-1,1',1"-triphenylmethane hexahydrobromide dihydrate;
3,3'-bis{[3,7,11,17-tetraaza-dicyclo[11.3.1]heptadecan-1 (16),13(17),14-trien-7-yl]-methyl}-4"-fluoro-1,1',1"-triphenylmethane hexahydrobromide dihydrate;
3,3'-bis{[3,7,11,17-tetraaza-dicyclo[11.3.1]heptadecan-1 (16),13(17),14-trien-7-yl]-methyl}-3"-chloro-1,1',1"-triphenylmethane hexahydrobromide dihydrate;
2-{[3,3'-bis((3,7,11,17-tetraaza-dicyclo[11.3.1]heptadecan-1(16),13(17),14-trien-7-yl)-methyl)-1,1'yl]-diphenyl}methylene pyridine hexahydrobromide dihydrate;
4,4'-bis{[3,7,11-triaza-dicyclo[11.3.1]heptadecan-1(16), 13(17),14-trien-7-yl]-methyl}-1,1',1"-triphenylmethane hexahydrobromide dihydrate;
4,4'-bis{[3,7,11-triaza-dicyclo[11.3.1]heptadecan-1(16), 13(17),14-trien-7-yl]-methyl}-4"-methyl-1,1',1"-triphenylmethane hexahydrobromide dihydrate;
4,4'-bis{[3,7,11-triaza-dicyclo[11.3.1]heptadecan-1(16), 13(17),14-trien-7-yl]-methyl}-4"-bromo-1,1',1"-triphenylmethane hexahydrobromide dihydrate;
4,4'-bis{[3,7,11-triaza-dicyclo[11.3.1]heptadecan-1(16), 13(17),14-trien-7-yl]-methyl}-4"-fluoro-1,1',1"-triphenylmethane hexahydrobromide dihydrate;
4,4'-bis{[3,7,11-triaza-dicyclo[11.3.1]heptadecan-1(16), 13(17),14-trien-7-yl]-methyl}-3"-chloro-1,1',1"-triphenylmethane hexahydrobromide dihydrate;
4,4'-bis{[3,7,11,17-tetraaza-dicyclo[11.3.1]heptadecan-1 (16),13(17),14-trien-7-yl]-methyl}-1,1',1"-triphenylmethane; hexahydrobromide dihydrate 4,4'-bis{[3,7,11, 17-tetraaza-dicyclo[11.3.1]heptadecan-1(16),13(17), 14-trien-7-yl]-methyl}-4''-methyl-1,1',1''-triphenylmethane hexahydrobromide dihydrate;

4,4'-bis{[3,7,11,17-tetraaza-dicyclo[11.3.1]heptadecan-1 (16),13(17),14-trien-7-yl]-methyl}-4''-bromo-1,1',1''-triphenylmethane hexahydrobromide dihydrate;

4,4'-bis{[3,7,11,17-tetraaza-dicyclo[11.3.1]heptadecan-1 (16),13(17),14-trien-7-yl]-methyl}-4''-fluoro-1,1',1''-triphenylmethane hexahydrobromide dihydrate; and 4,4'-bis{[3,7,11,17-tetraaza-dicyclo[11.3.1]heptadecan-1 (16),13(17),14-trien-7-yl]-methyl}-3''-chloro-1,1',1''-triphenylmethane hexahydrobromide dihydrate.

5. A method for preparing the compound according to claim 1 comprising the steps of:

1) preparing an intermediate formula IV or V with (o or p)-bromobenzaldehyde as a starting material, including protecting aldehyde moiety, forming derivatives of triaryl benzoic alcohol by using halogen-metal exchange of an alkali metal organic reagent and reaction of aryl metal compounds and ester radical, the reduction of aldehyde being achieved by using acid, and then reducing the aldehyde into an alcohol with a reducer, bromating the alcohol with a bromide to produce an intermediate of formula IV or V;

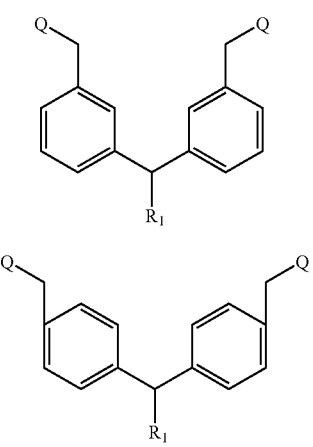

IV

V 2) preparing trisubstituted protected compound of formula VI with chain amine, this reaction including: sulfonylating the starting material with p-tosyl chloride, cyclizing with 1,2-di-p-tosyloxyethane, deprotecting with an acid, protecting with a protective group to prepare an intermediate compound of formula VI:

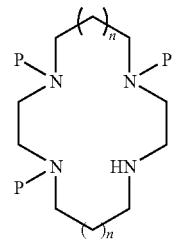

VI wherein n is 0 or 1, P is tosyl or trifluoroacetyl;

3) preparing a compound of formula VII with 3,3-iminodipropyl cyanide as starting material, including protecting the starting material with diethoxyphosphoryl, hydrogenating, protecting amino with p-tosyl, cyclizing with 1,3-dibromomethyl arene, and removing the protecting group diethoxyphosphoryl to obtain an intermediate compound of formula VII:

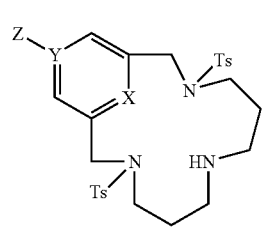

VII wherein, X, Y are carbon atom or oxygen atom, Z=H, Cl, Ph, OCH$_3$, and the like;

4) reacting the intermediate of formula IV or V and the intermediate of formula VI or VII in the presence of anhydrous K$_2$CO$_3$ in acetonitrile solvent to produce an intermediate compound of formula VIII, IX, X, or XI:

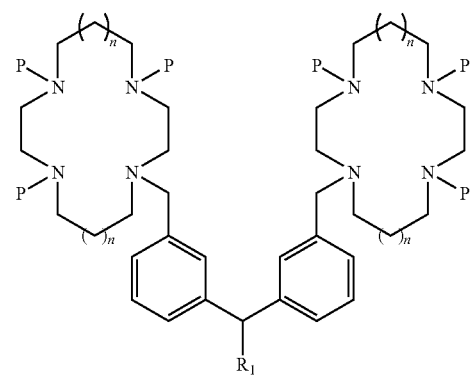

VIII

IX

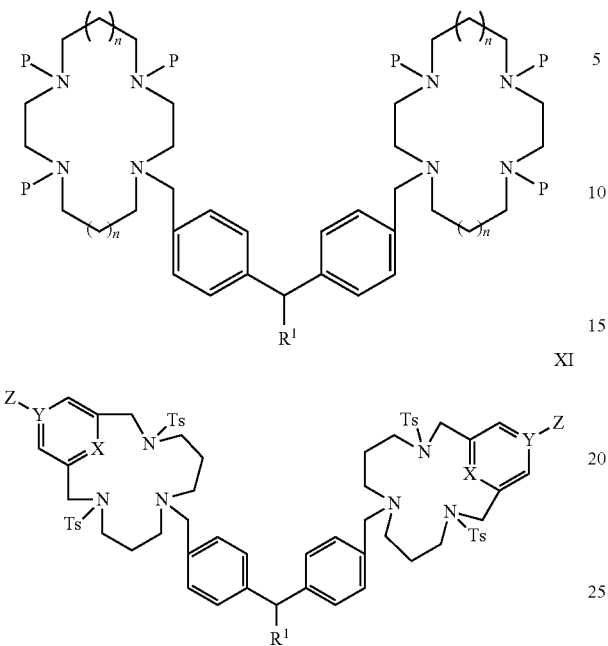

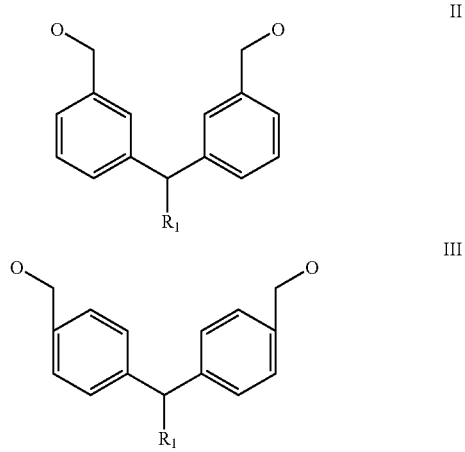

wherein, $R_1$ is as defined in formula I, P is p-tosyl or trifluoroacetyl; X, Y are carbon atom or nitrogen atom, Z=H, Cl, Ph, or $OCH_3$; and 5) when P is p-tosyl, deprotecting the compound of formula VIII, IX, X, or XI under acidic condition to form a salt; or when P is trifluoroacetyl, deprotecting the compound of formula VIII or X under basic condition, and then salifying, thereby forming an inorganic acid salt of the compound of formula II or the compound of formula III;

6. A pharmaceutical composition comprising the compound according to claim 1, an optical isomer, a pharmaceutically acceptable salt, or a hydrate thereof, and at least one pharmaceutically acceptable carrier, diluents, or excipient.

7. A method for treating a disease or disorder induced by HIV, comprising administering an effective amount of the compound according to claim 1 to a subject in need of this treatment.

* * * * *